United States Patent
Schoenmakers et al.

(10) Patent No.: US 8,912,329 B2
(45) Date of Patent: Dec. 16, 2014

(54) COMPOSITION FOR TREATMENT OF TUBERCULOSIS

(75) Inventors: Ronald Schoenmakers, Rijswijk (NL); Wilfried Weber, Freiburg (DE); Marc Gitzinger, Binningen (CH); Martin Fussenegger, Mägenwil (CH); Marcel Tigges, Bettingen (CH); Peter Schneider, Bottmingen (CH)

(73) Assignee: Bioversys AG, Basel (CH)

( * ) Notice: Subject to any disclaimer, the term of this patent is extended or adjusted under 35 U.S.C. 154(b) by 6 days.

(21) Appl. No.: 13/380,597

(22) PCT Filed: Jun. 25, 2010

(86) PCT No.: PCT/EP2010/059044
§ 371 (c)(1),
(2), (4) Date: Dec. 23, 2011

(87) PCT Pub. No.: WO2010/149761
PCT Pub. Date: Dec. 29, 2010

(65) Prior Publication Data
US 2012/0101080 A1    Apr. 26, 2012

(30) Foreign Application Priority Data
Jun. 25, 2009   (EP) .................................. 09163765

(51) Int. Cl.
| | | |
|---|---|---|
| *A61K 31/4965* | (2006.01) | |
| *C07D 295/108* | (2006.01) | |
| *C07D 413/02* | (2006.01) | |
| *C07D 413/06* | (2006.01) | |
| *A61K 31/167* | (2006.01) | |
| *A61K 45/06* | (2006.01) | |
| *A61K 31/443* | (2006.01) | |
| *A61K 31/4015* | (2006.01) | |
| *A61K 31/17* | (2006.01) | |
| *C07D 265/30* | (2006.01) | |
| *A61K 31/4439* | (2006.01) | |
| *A61K 31/496* | (2006.01) | |
| *C07D 207/12* | (2006.01) | |
| *C07D 241/04* | (2006.01) | |

(Continued)

(52) U.S. Cl.
CPC .......... *A61K 31/4015* (2013.01); *C07D 413/02* (2013.01); *C07D 413/06* (2013.01); *A61K 31/167* (2013.01); *A61K 45/06* (2013.01); *A61K 31/443* (2013.01); *A61K 31/17* (2013.01); *C07D 265/30* (2013.01); *A61K 31/4439* (2013.01); *A61K 31/496* (2013.01); *C07D 207/12* (2013.01); *C07D 241/04* (2013.01); *A61K 31/397* (2013.01); *C07D 207/08* (2013.01); *C07D 295/185* (2013.01); *A61K 31/341* (2013.01); *C07D 401/06* (2013.01); *C07D 205/04* (2013.01); *A61K 31/40* (2013.01); *A61K 31/5377* (2013.01); *C07D 213/74* (2013.01); *A61K 31/44* (2013.01); *C07D 213/38* (2013.01); *C07D 413/04* (2013.01); *A61K 31/7008* (2013.01); *A61K 31/5375* (2013.01); *C07D 307/32* (2013.01); *A61K 31/495* (2013.01)
USPC ....... 544/399; 548/540; 514/252.12; 514/676

(58) Field of Classification Search
USPC ............... 514/676, 252.12; 548/540; 544/399
See application file for complete search history.

(56) References Cited

U.S. PATENT DOCUMENTS

2009/0163545 A1*   6/2009   Goldfarb ........................ 514/312

FOREIGN PATENT DOCUMENTS

| EP | 2 072 038 | 6/2009 |
| GB | 872 488 | 7/1961 |

(Continued)

OTHER PUBLICATIONS

EP 2 072 028 Kropke, et al. (Jun. 24, 2009).*

(Continued)

*Primary Examiner* — Yong Chu
*Assistant Examiner* — Sonya Wright
(74) *Attorney, Agent, or Firm* — Wenderoth, Lind & Ponack, L.L.P.

(57) ABSTRACT

The invention relates to a pharmaceutical composition comprising a compound of formula (1) wherein $R^1$ is optionally substituted phenyl, optionally substituted pyridyl or optionally substituted indolyl; $R^2$ is $(CH_2)_n$ wherein n is 0, 1, 2, 3 or 4; $R^3$ is $(CH_2)_m R^{3.4}$ wherein m is 0, 1, 2, 3 or 4, and $R^{3.4}$ is methyl, isopropyl, tert-butyl, $OCH_3$, OH, optionally substituted phenoxy, C≡CH, C≡N, optionally substituted phenyl, furanyl or thienyl; A is a ring containing $X^1$ with the meaning O, S, NH, $N(CH_3)$ or $CH_2$; and $X^2$ is O, S or NH; and a compound of formula (2) wherein $R^4$ is optionally substituted phenyl, optionally substituted pyridyl, optionally substituted indolyl, —$NR^7R^8$; or —NH—N=CH—$R^9$; and substituents $R^5$ to $R^9$ have the meanings indicated in the description, in particular ethionamide. The pharmaceutical composition is useful, e.g., in the treatment of multidrug-resistant tuberculosis.

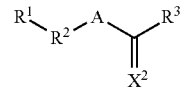

1

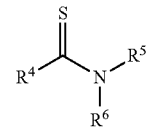

2

15 Claims, No Drawings

(51) Int. Cl.

| | |
|---|---|
| *A61K 31/397* | (2006.01) |
| *C07D 207/08* | (2006.01) |
| *C07D 295/185* | (2006.01) |
| *A61K 31/341* | (2006.01) |
| *C07D 401/06* | (2006.01) |
| *C07D 205/04* | (2006.01) |
| *A61K 31/40* | (2006.01) |
| *A61K 31/5377* | (2006.01) |
| *C07D 213/74* | (2006.01) |
| *A61K 31/44* | (2006.01) |
| *C07D 213/38* | (2006.01) |
| *C07D 413/04* | (2006.01) |
| *A61K 31/7008* | (2006.01) |
| *A61K 31/5375* | (2006.01) |
| *C07D 307/32* | (2006.01) |
| *A61K 31/495* | (2006.01) |

(56) References Cited

FOREIGN PATENT DOCUMENTS

| | | |
|---|---|---|
| WO | 01/56974 | 8/2001 |
| WO | 2005/108360 | 11/2005 |
| WO | 2008/003861 | 1/2008 |
| WO | 2009/080432 | 7/2009 |

OTHER PUBLICATIONS

STN results, U.S. 2009/0163545, Goldfarb, 2009.*
International Search Report issued Aug. 3, 2010 in International (PCT) Application No. PCT/EP2010/059044, of which the present application is the national stage.
Written Opinion issued Aug. 3, 2010 in International (PCT) Application No. PCT/EP2010/059044, of which the present application is the national stage.
E. Testa et al., "Substances acting on the central nervous system. XXII. 2-Phenylazetidine and derivatives", Justus Liebigs Annalen Der Chemie, vol. 656, pp. 114-119, 1962.
N. Willand et al., "Synthetic EthR inhibitors boost antituberculous activity of ethionamide", Nature Medicine, vol. 15, No. 5, pp. 537-544, 2009.
F. Frenois et al., "Structure of EthR in a Ligand Bound Conformation Reveals Therapeutic Perspectives against Tuberculosis", Molecular Cell, vol. 16, pp. 301-307, 2004.
W. Weber et al., "A synthetic mammalian gene circuit reveals antituberculosis compounds", PNAS, vol. 105, No. 29, pp. 9994-9998, 2008.
G. Zhu et al., "Template Effect of Pd(II) in the Synthesis of Differently Substituted Enantiopure γ-Butyrolactones and Its Synthetic Applications", Tetrahedron: Asymmetry, vol. 6, No. 7, pp. 1657-1666, 1995.
C. Copéret et al., "Cyclic Carbopalladation of Alkynes Terminated by Carbonylative Amidation", Tetrahedron, vol. 52, No. 35, pp. 11529-11544, 1996.
R. Borne et al., "Synthesis and Cholinergic Activity of Some Structural Analogs of Pilocarpine", Journal of Medicinal Chemistry, vol. 16, No. 3, pp. 245-247, 1973.
J. Belletire et al., "Dianion-Based Methodology for the Preparation of 2,3-Disubstituted Butyrolactones", Synthetic Communications, vol. 19, No. 19, pp. 3371-3378, 1989.
Y. Takigawa et al., "Construction of nitrogen-heterocyclic compounds through zirconium mediated intramolecular alkene-carbonyl coupling reaction of *N*-(*o*-alkenylaryl)carbamate derivatives", Tetrahedron, vol. 60, pp. 1385-1392, 2004.
E. Testa et al., "Substances acting on the central nervous system. XVIII. 3-Phenylazetidine", Justus Liebigs Annalen Der Chemie, vol. 639, pp. 157-165, 1961.

* cited by examiner

COMPOSITION FOR TREATMENT OF TUBERCULOSIS

FIELD OF THE INVENTION

The invention relates to pharmaceutical compositions useful in the treatment of tuberculosis and related diseases.

BACKGROUND OF THE INVENTION

Up to 9 million people contract tuberculosis every year and 50 million people are presently infected with *Mycobacterium tuberculosis* resistant to both first-line drugs isoniazid and rifampicin (WHO, Fact sheet No. 104, March 2007). Ethionamide (2-ethylthioiso-nicotinamide, 2-ethylpyrimidine-4-carbothioamide), a structural analogue of isoniazid, is currently the last line of defence in the treatment of multi-drug-resistant tuberculosis (MDR-TB). During 35 years of its clinical use, ethionamide has fortunately elicited little cross-resistance with isoniazid as both prodrugs have to be activated by different mycobacterial enzymes to develop their antimicrobial activity. Yet, ethionamide continues to be prescribed at hepatotoxic doses as a consequence of EthR repressing ethA, the monooxigenase that catalyses activation of the prodrug ethionamide into an anti-mycobacterial nicotinamide adenine dinucleotide derivative. Up to a 1 g/day are required for an acceptable concentration in blood (Holdiness, M. R., Clin Pharmacokinet 1984, 9, 511-44), which is associated with severe side-effects including neurotoxicity and fatal hepatotoxicity.

WO 2008/003861 describes compounds having a potentiating effect on the activity of ethionamide in the treatment of tuberculosis and related diseases. The present inventors have found that 2-phenylethyl butyrate, a licensed food additive, and related compounds potentiate the activity of thioamides or thioureas, e.g. ethionamide, in the treatment of tuberculosis (WO 2009/080432).

SUMMARY OF THE INVENTION

The invention relates to a pharmaceutical composition comprising a compound of formula wherein $R^1$ is

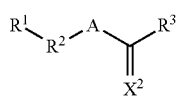

(1)

unsubstituted phenyl or phenyl substituted by one, two or three substituents selected from $C_1$-$C_6$-alkyl, trifluoromethyl, $C_1$-$C_6$-alkoxy, $C_1$-$C_6$-alkylcarbonyl, $C_1$-$C_6$-alkylcarbonyloxy, $C_1$-$C_6$-alkylthio, nitro, amino, $C_1$-$C_6$-alkylamino, di-$C_1$-$C_6$-alkylamino, pyrrolidino, piperidino, morpholino, $C_1$-$C_6$-alkylcarbonylamino, and halogen;

unsubstituted 2-, 3- or 4-pyridyl or 2-, 3- or 4-pyridyl substituted by one or two substituents selected from $C_1$-$C_6$-alkyl, trifluoromethyl, $C_1$-$C_6$-alkoxy, nitro, amino, $C_1$-$C_6$-alkylamino, di-$C_1$-$C_6$-alkylamino, $C_1$-$C_6$-alkylcarbonylamino, and halogen; or unsubstituted indolyl or indolyl substituted by one or two substituents selected from $C_1$-$C_6$-alkyl, trifluoromethyl, $C_1$-$C_6$-alkoxy, nitro, amino, $C_1$-$C_6$-alkylamino, di-$C_1$-$C_6$-alkylamino, $C_1$-$C_6$-alkylcarbonylamino, and halogen;

$R^2$ is $(CH_2)_n$ wherein n is 0, 1, 2, 3 or 4;

$R^3$ is $(CH_2)_m R^{3A}$ wherein m is 0, 1, 2, 3 or 4;

$R^{3A}$ is $CH_3$, $CH(CH_3)_2$; $C(CH_3)_3$, $OCH_3$, OH, $OR^{3B}$, C≡CH, C≡N, unsubstituted phenyl or phenyl substituted by one, two or three substituents selected from $C_1$-$C_6$-alkyl, trifluoromethyl, $C_1$-$C_6$-alkoxy, $C_1$-$C_6$-alkylcarbonyl, $C_1$-$C_6$-alkylcarbonyloxy, $C_1$-$C_6$-alkylthio, nitro, amino, $C_1$-$C_6$-alkylamino, di-$C_1$-$C_6$-alkylamino, pyrrolidino, piperidino, morpholino, $C_1$-$C_6$-alkylcarbonylamino, and halogen;

unsubstituted 2- or 3-furanyl or 2- or 3-furanyl substituted by one or two substituents selected from $C_1$-$C_6$-alkyl, trifluoromethyl, $C_1$-$C_6$-alkoxy, and halogen; or unsubstituted 2- or 3-thienyl or 2- or 3-thienyl substituted by one or two substituents selected from $C_1$-$C_6$-alkyl, trifluoromethyl, $C_1$-$C_6$-alkoxy, and halogen; and wherein $R^{3B}$ is unsubstituted phenyl or phenyl substituted by one, two or three substituents selected from $C_1$-$C_6$-alkyl, trifluoromethyl, $C_1$-$C_6$-alkoxy, $C_1$-$C_6$-alkylcarbonyl, $C_1$-$C_6$-alkylcarbonyloxy, $C_1$-$C_6$-alkylthio, nitro, amino, $C_1$-$C_6$-alkylamino, di-$C_1$-$C_6$-alkylamino, pyrrolidino, piperidino, morpholino, $C_1$-$C_6$-alkylcarbonylamino, and halogen;

A is selected from

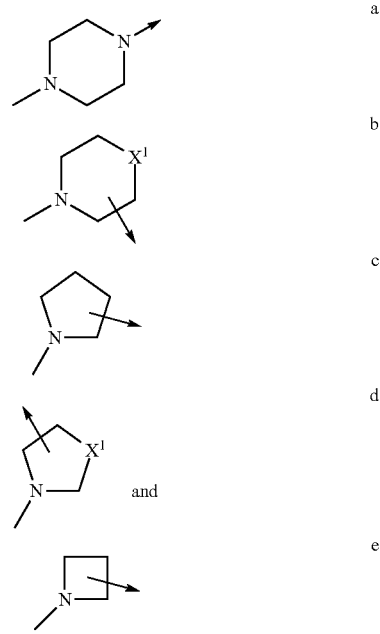

wherein - represents the bond to $C(=X^2)$—$R^3$ and → represents the bond to $R^2$—$R^1$;

or A together with —$C(=X^2)$—$R^3$ forms a ring

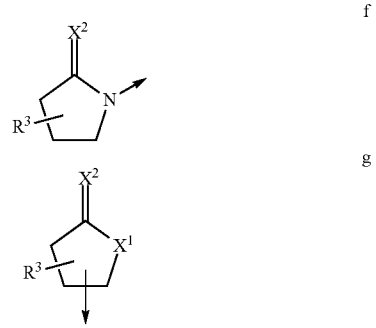

-continued

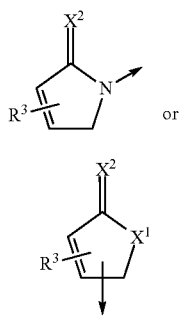

wherein → represents the bond to $R^2$—$R^1$;
$X^1$ is O, S, NH, N(CH$_3$) or CH$_2$; and
$X^2$ is O, S or NH.
and a compound of formula

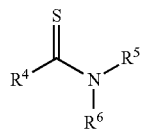

2 wherein $R^4$ is optionally substituted phenyl, optionally substituted pyridyl, optionally substituted indolyl, —$NR^7R^8$, or —NH—N=CH—$R^9$;
$R^5$ is hydrogen, $C_1$-$C_6$-alkyl, optionally substituted phenyl, optionally substituted pyridyl, or a sugar residue;
$R^6$ is hydrogen or $C_1$-$C_6$-alkyl, or $R^5$ and $R^6$ together with the N-atom to which they are bound are pyrrolidine, piperidine or morpholine;
$R^7$ is hydrogen, $C_1$-$C_6$-alkyl, optionally substituted phenyl, optionally substituted pyridyl, or a sugar residue;
$R^8$ is hydrogen or $C_1$-$C_6$-alkyl, or $R^7$ and $R^8$ together with the N-atom to which they are bound are pyrrolidine, piperidine or morpholine; and
$R^9$ is optionally substituted phenyl.

Most preferred is a composition comprising a compound of formula 1 and a compound of formula 2 selected from ethionamide, isoxyl, N-arabinofuranosyl-N'-[p-(isoamyloxy)phenyl]-thiourea or thiacetazone, in particular ethionamide.

The invention also relates to new compounds of formula 1 as defined hereinbefore.

The invention likewise relates to the use of a composition comprising a compound of formula 1 and of formula 2, e.g. ethionamide, in the treatment of tuberculosis and related diseases, and to a method of treatment of tuberculosis and related diseases wherein a composition comprising a compound of formula 1 and of formula 2, e.g. ethionamide, is applied.

DETAILED DESCRIPTION OF THE INVENTION

The invention relates to a pharmaceutical composition comprising a compound of formula 1 and a compound of formula 2 as defined hereinafter. The invention is based on the observation that a compound preventing EthR from binding to the ethA promoter substantially increases the activity of ethionamide, but also of other thioamides or thioureas, in the treatment of tuberculosis. A synthetic network in mammalian cells can be used to screen for compounds that prevent EthR-VP16 from binding to its cognate operator site ($O_{ethR}$-$P_{hsp70min}$) and thus transactivate the expression of the reporter gene (SEAP). Active compounds remove the EthR protein from the hybrid promoter and thus inhibit further expression of the reporter gene SEAP. This assay proved to be very stringent in the identification of active compounds, and the determined minimal inhibitory concentrations are in good agreement with respective results from ELISA screens and screens in microbial pathogens. The results of the mammalian synthetic screening network therefore proved to be highly compatible with the observed endogenous resistance regulatory networks in pathogenic backgrounds (WO 2009/080432; Weber et al., PNAS 2008, 105, 9994-8).

It has now been found that compounds of formula

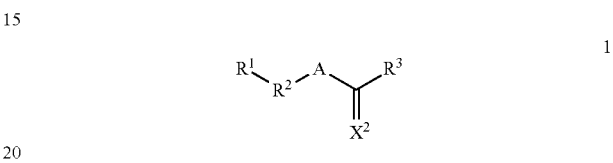

1 wherein $R^1$ is
unsubstituted phenyl or phenyl substituted by one, two or three substituents selected from $C_1$-$C_6$-alkyl, trifluoromethyl, $C_1$-$C_6$-alkoxy, $C_1$-$C_6$-alkylcarbonyl, $C_1$-$C_6$-alkylcarbonyloxy, $C_1$-$C_6$-alkylthio, nitro, amino, $C_1$-$C_6$-alkylamino, di-$C_1$-$C_6$-alkylamino, pyrrolidino, piperidino, morpholino, $C_1$-$C_6$-alkylcarbonylamino, and halogen;
unsubstituted 2-, 3- or 4-pyridyl or 2-, 3- or 4-pyridyl substituted by one or two substituents selected from $C_1$-$C_6$-alkyl, trifluoromethyl, $C_1$-$C_6$-alkoxy, nitro, amino, $C_1$-$C_6$-alkylamino, di-$C_1$-$C_6$-alkylamino, $C_1$-$C_6$-alkylcarbonylamino, and halogen; or
unsubstituted indolyl or indolyl substituted by one or two substituents selected from $C_1$-$C_6$-alkyl, trifluoromethyl, $C_1$-$C_6$-alkoxy, nitro, amino, $C_1$-$C_6$-alkylamino, di-$C_1$-$C_6$-alkylamino, $C_1$-$C_6$-alkylcarbonylamino, and halogen;
$R^2$ is $(CH_2)_n$ wherein n is 0, 1, 2, 3 or 4;
$R^3$ is $(CH_2)_m R^{3A}$ wherein m is 0, 1, 2, 3 or 4;
$R^{3A}$ is $CH_3$, $CH(CH_3)_2$; $C(CH_3)_3$, $OCH_3$, OH, $OR^{3B}$, C≡CH, C≡N,
unsubstituted phenyl or phenyl substituted by one, two or three substituents selected from $C_1$-$C_6$-alkyl, trifluoromethyl, $C_1$-$C_6$-alkoxy, $C_1$-$C_6$-alkylcarbonyl, $C_1$-$C_6$-alkylcarbonyloxy, $C_1$-$C_6$-alkylthio, nitro, amino, $C_1$-$C_6$-alkylamino, di-$C_1$-$C_6$-alkylamino, pyrrolidino, piperidino, morpholino, $C_1$-$C_6$-alkylcarbonylamino, and halogen;
unsubstituted 2- or 3-furanyl or 2- or 3-furanyl substituted by one or two substituents selected from $C_1$-$C_6$-alkyl, trifluoromethyl, $C_1$-$C_6$-alkoxy, and halogen; or
unsubstituted 2- or 3-thienyl or 2- or 3-thienyl substituted by one or two substituents selected from $C_1$-$C_6$-alkyl, trifluoromethyl, $C_1$-$C_6$-alkoxy, and halogen; and wherein
$R^{3B}$ is unsubstituted phenyl or phenyl substituted by one, two or three substituents selected from $C_1$-$C_6$-alkyl, trifluoromethyl, $C_1$-$C_6$-alkoxy, $C_1$-$C_6$-alkylcarbonyl, $C_1$-$C_6$-alkylcarbonyloxy, $C_1$-$C_6$-alkylthio, nitro, amino, $C_1$-$C_6$-alkylamino, di-$C_1$-$C_6$-alkylamino, pyrrolidino, piperidino, morpholino, $C_1$-$C_6$-alkylcarbonylamino, and halogen;
A is selected from

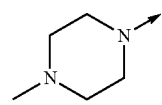

a

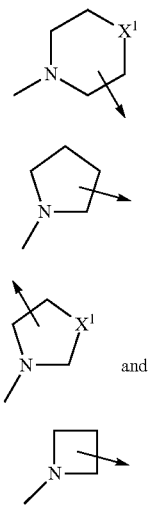

wherein - represents the bond to C(=X²)—R³ and → represents the bond to R²—R¹;
or A together with —C(=X²)—R³ forms a ring

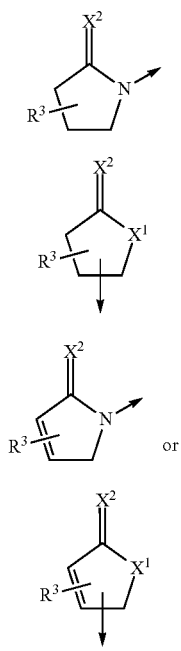

wherein → represents the bond to R²—R¹;
$X^1$ is O, S, NH, N(CH₃) or CH₂; and
$X^2$ is O, S or NH;
are useful as compounds preventing EthR from binding to the ethA promoter. The invention therefore relates to a pharmaceutical composition comprising such compounds of formula 1 together with a compound of formula 2.

In the presentation of partial structures a to i for A, bonds presented as - or → not localised at a particular ring position indicate that such bond may be connected to any position of the ring representing a carbon atom not yet fully substituted. For example, in partial structure f, the bond carrying R³ may be located in any of the ring carbon positions except the carbon carrying =X².

Compounds of formula 2

$$\underset{R^4}{\overset{S}{\|}} \underset{\underset{R^6}{|}}{N} - R^5 \qquad 2$$

in the pharmaceutical composition according to the invention are those wherein
$R^4$ is optionally substituted phenyl, optionally substituted pyridyl, optionally substituted indolyl, —NR⁷R⁸, or —NH—N=CH—R⁹;
$R^5$ is hydrogen, $C_1$-$C_6$-alkyl, optionally substituted phenyl, optionally substituted pyridyl, or a sugar residue;
$R^6$ is hydrogen or $C_1$-$C_6$-alkyl, or R⁵ and R⁶ together with the N-atom to which they are bound are pyrrolidine, piperidine or morpholine;
$R^7$ is hydrogen, $C_1$-$C_6$-alkyl, optionally substituted phenyl, optionally substituted pyridyl, or a sugar residue;
$R^8$ is hydrogen or $C_1$-$C_6$-alkyl, or R⁷ and R⁸ together with the N-atom to which they are bound are pyrrolidine, piperidine or morpholine; and
$R^9$ is optionally substituted phenyl.

The general terms used hereinbefore and hereinafter preferably have within the context of this disclosure the following meanings, unless otherwise indicated:

Alkyl is in particular $C_1$-$C_6$-alkyl, for example $C_1$-$C_4$-alkyl. $C_1$-$C_4$-Alkyl is methyl, ethyl, propyl, e.g. n-propyl or iso-propyl, or butyl, e.g. n-butyl, iso-butyl or tert-butyl. $C_1$-$C_6$-Alkyl is methyl, ethyl, propyl or butyl as described, or also pentyl, e.g. n-pentyl or iso-pentyl, or hexyl, e.g. n-hexyl or iso-hexyl.

Optionally substituted phenyl is unsubstituted phenyl or phenyl substituted by one, two or three substituents selected from $C_1$-$C_6$-alkyl, e.g. methyl, trifluoromethyl, $C_1$-$C_6$-alkoxy, e.g. methoxy, ethoxy or iso-pentoxy, $C_1$-$C_6$-alkylcarbonyl, e.g. acetyl, $C_1$-$C_6$-alkyl-carbonyloxy, e.g. acetoxy, $C_1$-$C_6$-alkylthio, e.g. methylthio, nitro, amino, $C_1$-$C_6$-alkylamino, e.g. methylamino or ethylamino, di-$C_1$-$C_6$-alkylamino, e.g. dimethylamino or diethylamino, pyrrolidino, piperidino, morpholino, $C_1$-$C_6$-alkylcarbonylamino, e.g. acetylamino, and halogen. Halogen is fluoro, chloro, bromo or iodo, particularly fluoro or chloro. Preferably optionally substituted phenyl is phenyl or phenyl substituted by one or two of the mentioned substituents, in particular one of the mentioned substituents in ortho, meta or para position, preferably in meta or para position. For example, optionally substituted phenyl is phenyl, methyl- or dimethylphenyl, trifluoromethylphenyl, methoxyphenyl, ethoxyphenyl, acetoxyphenyl, nitrophenyl, dinitrophenyl, aminophenyl, methylamino-phenyl, dimethylaminophenyl, fluorophenyl, chlorophenyl or dichlorophenyl.

Optionally substituted pyridyl is 2-, 3- or 4-pyridyl, unsubstituted or substituted by one or two substituents selected from $C_1$-$C_6$-alkyl, e.g. methyl or ethyl, trifluoromethyl, $C_1$-$C_6$-alkoxy, e.g. methoxy or ethoxy, nitro, amino, $C_1$-$C_6$-alkylamino, e.g. methylamino or ethylamino, di-$C_1$-$C_6$-alkylamino, e.g. dimethylamino or diethylamino, $C_1$-$C_6$-alkylcarbonylamino, e.g. acetylamino, and halogen. Halogen is fluoro, chloro, bromo or iodo, particularly fluoro or chloro.

Optionally substituted indolyl is 1H-2-, 3-, 4-, 5-, 6-, or 7-indolyl, unsubstituted or substituted by one or two substituents selected from $C_1$-$C_6$-alkyl, e.g. methyl or ethyl, trifluoromethyl, $C_1$-$C_6$-alkoxy, e.g. methoxy or ethoxy, nitro, amino, $C_1$-$C_6$-alkylamino, e.g. methylamino or ethylamino, di-$C_1$-$C_6$-alkylamino, e.g. dimethylamino or diethylamino, $C_1$-$C_6$-alkylcarbonylamino, e.g. acetylamino, and halogen.

Optionally substituted furanyl is 2- or 3-furanyl, unsubstituted or substituted by one or two substituents selected from $C_1$-$C_6$-alkyl, e.g. methyl or ethyl, trifluoromethyl, $C_1$-$C_6$-alkoxy, e.g. methoxy or ethoxy, and halogen, e.g. fluoro, chloro, bromo or iodo, particularly fluoro or chloro.

Optionally substituted thienyl is 2- or 3- thienyl, unsubstituted or substituted by one or two substituents selected from $C_1$-$C_6$-alkyl, e.g. methyl or ethyl, trifluoromethyl, $C_1$-$C_6$-alkoxy, e.g. methoxy or ethoxy, and halogen, e.g. fluoro, chloro, bromo or iodo, particularly fluoro or chloro.

A sugar residue is
L- or D-furanosyl selected from the aldopentoses arabinose, lyxose, ribose and xylose of formula 3;
L- or D-hexofuranosyl selected from the aldohexoses allose, altrose, glucose, mannose, gulose, idose, galactose and talose of formula 4;
L- or D-hexofuranosyl selected from the ketohexoses fructose, psicose, sorbose and tagatose of formula 5;
L- or D-pyranosyl selected from the aldohexoses allose, altrose, glucose, mannose, gulose, idose, galctose and talose of formula 6; or
L- or D-pyranosyl selected from the ketohexoses fructose, psicose, sorbose and tagatose of formula 7;

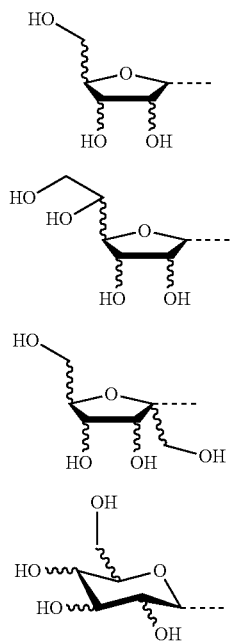

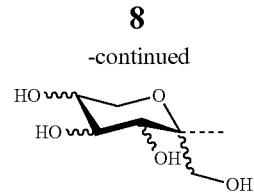

in which one, two, three or four hydroxy groups can be methylated, benzylated or acetylated, or one hydroxy group can be replaced by hydrogen, halogen, methylamino, ethylamino, or acetamido.

As mentioned above, compounds of formula 1 have valuable properties. These properties are determined with the following test:

Clonal populations of a cell line stably expressing pWW489 and pWW491 (Weber et al., PNAS 2008, 105, 9994-8) are treated with varying amounts of the respective compounds displayed in Table 1. 48 hours after addition of compounds or solvent (w/o) the supernatants containing the secreted reporter protein SEAP are analyzed. SEAP levels of untreated condition (w/o) are set to 100%. Table 1 summarizes the relative EthR-VP16 activity reflected by SEAP expression in the presence of the respective compound at different concentrations, ranging from 500 nMol (0.5) to 300 µMol (300).

Growth of M. tuberculosis is significantly impaired in the presence of ethionamide due to EthA-mediated conversion of this prodrug into an antimycobacterial nicotinamide adenine dinucleotide derivative. EthR-mediated repression of ethA transcription requires rather high clinical doses of ethionamide (up to 1 g/day, Holdiness, M. R., Clin Pharmacokinet 1984, 9, 511-44), which is associated with severe side-effects including neurotoxicity and fatal hepatotoxicity, yet is often still insufficient to reach minimum inhibitory levels in the blood stream. Therefore, 2-phenylethyl butyrate-triggered dissociation of EthR from the ethA promoter resulting in de-repression of ethA increases the sensitivity of *Mycobacterium* to ethionamide-based therapy. Growth of *M. tuberculosis* H37Rv in the presence of sub-inhibitory ethionamide concentrations (0.16 and 5 μg/ml), which are easily reached by therapeutic doses, ($c_{max}$[250 mg oral]=2 μg/ml, $t_{1/2}$=2 h) is dose-dependently inhibited by 0.5 to 40.5 μMol 2-(4-Fluorophenoxy)-1-(3-phenylpyrrolidin-1-yl)ethan-1-one (compound of Example 15), 3-Phenyl-1-(3-phenylpyrrolidin-1-yl) propan-1-one (compound of Example 16) and 2-Phenyl-1-(3-phenylpyrrolidin-1-yl)ethan-1-one (compound of Example 17), see Table 2. Since these three compounds alone do not show any growth inhibitory effect, the compounds must act synergistically with ethionamide to kill the pathogen.

TABLE 1

Dose response curve of selected compounds on EthR-VP16 mediated gene regulation in $_{EthR}$HEK-SEAP cells.

| Example | % EthR activity (w/o = 100%); ± std. dev. of the mean (n = 3) μM | | | | | | | |
|---|---|---|---|---|---|---|---|---|
| No. | 0.5 | 1.5 | 3 | 6 | 15 | 30 | 60 | 300 |
| 1 | 72.52 ± 1.65 | 76.47 ± 17.47 | 68.72 ± 2.79 | 73.21 ± 1.19 | 72.61 ± 6.82 | 64.08 ± 14.0 | 53.06 ± 7.78 | 27.31 ± 5.27 |
| 3 | 85.48 ± 2.57 | 96.82 ± 0.67 | 84.40 ± 6.37 | 90.09 ± 6.44 | 98.44 ± 4.51 | 86.46 ± 4.10 | 81.94 ± 8.60 | 40.24 ± 4.65 |
| 13 | 30.37 ± 3.98 | 17.73 ± 2.01 | 11.00 ± 2.88 | 10.86 ± 1.45 | 12.40 ± 0.99 | 14.48 ± 7.80 | 10.82 ± 1.34 | 11.97 ± 1.27 |
| 14 | 106.06 ± 19.75 | 86.17 ± 1.36 | 85.88 ± 6.26 | 74.80 ± 1.22 | 60.55 ± 1.32 | 35.37 ± 5.30 | 25.48 ± 3.82 | 9.16 ± 1.37 |
| 15 | 10.33 ± 1.26 | 10.27 ± 0.43 | 7.81 ± 0.95 | 6.01 ± 1.93 | 3.21 ± 1.35 | 0.77 ± 0.32 | 0.86 ± 0.36 | 0.89 ± 0.37 |

TABLE 1-continued

Dose response curve of selected compounds on EthR-VP16 mediated gene regulation in $_{EthR}$HEK-SEAP cells.

| Example No. | % EthR activity (w/o = 100%); ± std. dev. of the mean (n = 3) μM | | | | | | | |
|---|---|---|---|---|---|---|---|---|
| | 0.5 | 1.5 | 3 | 6 | 15 | 30 | 60 | 300 |
| 16 | 28.34 ± 1.26 | 27.24 ± 0.46 | 19.93 ± 0.43 | 13.49 ± 2.96 | 11.82 ± 2.60 | 11.41 ± 2.51 | 2.82 ± 0.62 | 0.85 ± 0.18 |
| 17 | 38.51 ± 8.47 | 35.51 ± 7.81 | 22.46 ± 4.94 | 16.27 ± 3.58 | 14.23 ± 3.13 | 11.47 ± 8.52 | 1.86 ± 0.40 | 0.83 ± 0.18 |
| 18 | 91.94 ± 3.57 | 80.73 ± 8.89 | 81.37 ± 15.91 | 59.33 ± 1.20 | 44.16 ± 2.35 | 11.20 ± 1.68 | 12.36 ± 1.85 | 1.74 ± 0.26 |
| 19 | 95.57 ± 9.07 | 102.06 ± 4.13 | 95.94 ± 9.02 | 96.36 ± 13.48 | 75.95 ± 6.56 | 35.25 ± 5.28 | 33.46 ± 5.96 | 27.55 ± 0.37 |
| 20 | 96.58 ± 11.13 | 90.87 ± 14.02 | 88.25 ± 8.63 | 89.00 ± 4.56 | 75.50 ± 6.63 | 43.71 ± 3.21 | 32.97 ± 6.41 | 35.52 ± 1.37 |
| 21 | 107.88 ± 7.36 | 98.48 ± 16.40 | 73.54 ± 7.58 | 60.17 ± 8.98 | 40.76 ± 4.81 | 8.33 ± 5.61 | 6.29 ± 1.05 | 1.34 ± 1.58 |
| 22 | 89.95 ± 15.21 | 106.44 ± 10.03 | 97.40 ± 5.01 | 90.22 ± 8.48 | 77.83 ± 4.33 | 59.41 ± 4.50 | 33.21 ± 2.46 | 6.34 ± 0.89 |
| 23 | 96.32 ± 10.01 | 102.15 ± 12.32 | 101.15 ± 9.55 | 90.08 ± 9.21 | 86.75 ± 5.76 | 81.55 ± 5.22 | 49.37 ± 1.49 | 6.18 ± 2.53 |
| 25 | 86.75 ± 9.98 | 88.46 ± 8.12 | 69.52 ± 4.27 | 48.03 ± 5.86 | 28.69 ± 3.22 | 19.46 ± 0.89 | 14.16 ± 3.23 | 6.03 ± 2.00 |
| 27 | 59.65 ± 2.49 | 42.65 ± 1.49 | 37.86 ± 5.47 | 31.30 ± 3.58 | 31.67 ± 1.36 | 26.30 ± 9.65 | 17.54 ± 4.51 | 15.31 ± 2.79 |
| 28 | 97.07 ± 9.36 | 81.47 ± 3.01 | 59.42 ± 4.90 | 46.16 ± 2.55 | 38.30 ± 2.21 | 18.54 ± 3.64 | 11.70 ± 2.77 | 10.25 ± 1.94 |
| 29 | 85.43 ± 9.96 | 55.95 ± 5.54 | 36.47 ± 3.17 | 26.52 ± 0.73 | 16.92 ± 0.73 | 16.66 ± 3.59 | 10.03 ± 2.93 | 12.93 ± 4.60 |
| 30 | 111.76 ± 16.15 | 111.21 ± 17.13 | 100.74 ± 5.87 | 90.45 ± 5.55 | 69.19 ± 8.71 | 43.33 ± 2.01 | 26.89 ± 2.34 | 14.87 ± 3.00 |
| 31 | 106.43 ± 17.54 | 103.41 ± 16.43 | 94.08 ± 15.93 | 63.68 ± 5.26 | 33.23 ± 1.27 | 24.99 ± 4.22 | 17.75 ± 4.01 | 14.98 ± 2.11 |
| 32 | 12.49 ± 5.97 | 10.68 ± 2.55 | 10.37 ± 2.69 | 9.96 ± 3.44 | 5.65 ± 1.10 | 8.77 ± 1.57 | 8.89 ± 1.74 | 1.56 ± 0.80 |
| 33 | 11.37 ± 3.47 | 14.88 ± 5.68 | 5.80 ± 2.33 | 3.83 ± 1.01 | 4.58 ± 1.34 | 5.01 ± 0.80 | 5.24 ± 2.58 | 2.78 ± 1.33 |

TABLE 2

Synergistic effect of ethionamide with compounds Examples 15, 16 and 17 on growth inhibition of *Mycobacterium tuberculosis* laboratory strain H37Rv

| | | Ethionamide concentration (μg/ml) | | | | | |
|---|---|---|---|---|---|---|---|
| | | 0 | 0.16 | 0.31 | 0.625 | 1.25 | 2.5 | 5 |
| Example No. 15 (μM) | 0 | R | R | R | R | R | I | S |
| | 0.5 | R | R | R | I | S | S | S |
| | 1.5 | R | R | I | I | S | S | S |
| | 4.5 | R | R | I | S | S | S | S |
| | 13.5 | R | R | I | S | S | S | S |
| | 40.5 | R | R | I | S | S | S | S |
| Example No. 16 (μM) | 0 | R | R | R | R | R | I | S |
| | 0.5 | R | R | R | I | S | S | S |
| | 1.5 | R | R | I | S | S | S | S |
| | 4.5 | R | R | I | S | S | S | S |
| | 13.5 | R | I | S | S | S | S | S |
| | 40.5 | R | I | I | S | S | S | S |
| Example No. 17 (μM) | 0 | R | R | R | R | R | I | S |
| | 0.5 | R | R | R | R | R | I | S |
| | 1.5 | R | R | R | R | I | S | S |
| | 4.5 | R | R | R | R | I | S | S |
| | 13.5 | R | R | R | I | I | S | S |
| | 40.5 | R | R | R | S | S | S | S |

(R: Resistance, no effect of combinatorial drug application; I: intermediate; S: sensitive)

Preferably the invention relates to pharmaceutical compositions comprising a compound of formula 1 designated as being preferred hereinafter and a compound of formula 2 designated as preferred hereinafter, and also to novel compounds of formula 1 designated as preferred hereinafter as such.

In particular, the invention concerns a pharmaceutical composition comprising a compound of formula 1 wherein $R^1$ is
unsubstituted phenyl or phenyl substituted by one, two or three substituents selected from $C_1$-$C_6$-alkyl, trifluoromethyl, $C_1$-$C_6$-alkoxy, $C_1$-$C_6$-alkylcarbonyl, $C_1$-$C_6$-alkylcarbonyloxy, $C_1$-$C_6$-alkylthio, nitro, amino, $C_1$-$C_6$-alkylamino, di-$C_1$-$C_6$-alkylamino, pyrrolidino, piperidino, morpholino, $C_1$-$C_6$-alkylcarbonylamino, and halogen;
unsubstituted 2-, 3- or 4-pyridyl or 2-, 3- or 4-pyridyl substituted by one or two substituents selected from $C_1$-$C_6$-alkyl, trifluoromethyl, $C_1$-$C_6$-alkoxy, nitro, amino, $C_1$-$C_6$-alkylamino, di-$C_1$-$C_6$-alkylamino, $C_1$-$C_6$-alkylcarbonylamino, and halogen; or
unsubstituted indolyl or indolyl substituted by one or two substituents selected from $C_1$-$C_6$-alkyl, trifluoromethyl, $C_1$-$C_6$-alkoxy, nitro, amino, $C_1$-$C_6$-alkylamino, di-$C_1$-$C_6$-alkylamino, $C_1$-$C_6$-alkylcarbonylamino, and halogen;
$R^2$ is $(CH_2)_n$ wherein n is 0, 1, 2, 3 or 4;
$R^3$ is $(CH_2)_mCH_3$, $(CH_2)_mOCH_3$, $(CH_2)_mOH$, $(CH_2)_mC\equiv CH$ or $(CH_2)_mC\equiv N$ wherein m is 0, 1, 2 or 3;
A is selected from partial structures a to d and f to i as defined above;
$X^1$ is O, S, NH, N(CH$_3$) or CH$_2$; and
$X^2$ is O, S or NH;
and a compound of formula 2 as defined above, e.g. a compound selected from ethionamide, isoxyl, N-arabinofuranosyl-N'-[p-(isoamyloxy)phenyl]-thiourea or thiacetazone, in particular the compound ethionamide.

Preferred compounds of formula 1 in the pharmaceutical compositions of the invention are those wherein
$R^1$ is unsubstituted phenyl or phenyl monosubstituted by one substituent selected from trifluoromethyl, $C_1$-$C_3$-alkoxy, $C_1$-$C_3$-alkylcarbonyl, $C_1$-$C_3$-alkylthio, nitro, amino, $C_1$-$C_3$-alkylamino, and halogen; unsubstituted 2-, 3- or 4-pyridyl or 2-, 3- or 4-pyridyl mono-substituted by one substituent selected from trifluoromethyl, $C_1$-$C_3$-alkoxy, nitro, amino, $C_1$-$C_3$-alkylamino, and halogen; or unsubstituted indolyl or indolyl monosubstituted by one substituent selected from trifluoromethyl, $C_1$-$C_3$-alkoxy, nitro, amino, $C_1$-$C_3$-alkylamino, and halogen;
$R^2$ is $(CH_2)_n$ wherein n is 0, 1 or 2;
$R^3$ is $(CH_2)_mR^{3A}$ wherein m is 0, 1, 2, 3 or 4;
$R^{3A}$ is $CH_3$, $CH(CH_3)_2$, $C(CH_3)_3$, $OCH_3$, $OH$, $OR^{3B}$, $C\equiv CH$, $C\equiv N$,
unsubstituted phenyl or phenyl substituted by one, two or three substituents selected from $C_1$-$C_6$-alkyl, trifluoromethyl, $C_1$-$C_6$-alkoxy, $C_1$-$C_6$-alkylcarbonyl, $C_1$-$C_6$-alkylcarbonyloxy, $C_1$-$C_6$-alkylthio, nitro, amino, $C_1$-$C_6$-alkylamino, di-$C_1$-$C_6$-alkylamino, pyrrolidino, piperidino, morpholino, $C_1$-$C_6$-alkylcarbonylamino, and halogen;
unsubstituted 2- or 3-furanyl or 2- or 3-furanyl substituted by one or two substituents selected from $C_1$-$C_6$-alkyl, trifluoromethyl, $C_1$-$C_6$-alkoxy, and halogen; or
unsubstituted 2- or 3-thienyl or 2- or 3-thienyl substituted by one or two substituents selected from $C_1$-$C_6$-alkyl, trifluoromethyl, $C_1$-$C_6$-alkoxy, and halogen; and wherein $R^{3B}$ is unsubstituted phenyl or phenyl substituted by one, two or three substituents selected from $C_1$-$C_6$-alkyl, trifluoromethyl, $C_1$-$C_6$-alkoxy, $C_1$-$C_6$-alkylcarbonyl, $C_1$-$C_6$-alkylcarbonyloxy, $C_1$-$C_6$-alkylthio, nitro, amino, $C_1$-$C_6$-alkylamino, di-$C_1$-$C_6$-alkylamino, pyrrolidino, piperidino, morpholino, $C_1$-$C_6$-alkylcarbonylamino, and halogen;

A is selected from partial structures a to i as defined above;

$X^1$ is O, S, NH, N($CH_3$) or $CH_2$; and $X^2$ is O, S or NH.

Equally preferred are compounds of formula 1 in the pharmaceutical compositions of the invention wherein $R^1$ is unsubstituted phenyl or phenyl monosubstituted by one substituent selected from $C_1$-$C_3$-alkyl, trifluoromethyl, $C_1$-$C_3$-alkoxy, $C_1$-$C_3$-alkylcarbonyl, $C_1$-$C_3$-alkylcarbonyloxy, $C_1$-$C_3$-alkylthio, nitro, amino, $C_1$-$C_3$-alkylamino, di-$C_1$-$C_3$-alkylamino, pyrrolidino, piperidino, morpholino, $C_1$-$C_3$-alkylcarbonylamino, and halogen; unsubstituted 2-, 3- or 4-pyridyl or 2-, 3- or 4-pyridyl monosubstituted by one substituent selected from $C_1$-$C_3$-alkyl, trifluoro methyl, $C_1$-$C_3$-alkoxy, nitro, amino, $C_1$-$C_3$-alkylamino, di-$C_1$-$C_3$-alkylamino, $C_1$-$C_3$-alkyl carbonylamino, and halogen; or unsubstituted indolyl or indolyl monosubstituted by one substituent selected from $C_1$-$C_3$-alkyl, trifluoromethyl, $C_1$-$C_3$-alkoxy, nitro, amino, $C_1$-$C_3$-alkylamino, di-$C_1$-$C_3$-alkylamino, $C_1$-$C_3$ alkylcarbonylamino, and halogen;

$R^2$ is $(CH_2)_n$ wherein n is 0, 1 or 2;

$R^3$ is $(CH_2)_m R^{3A}$ wherein m is 0, 1, 2, 3 or 4;

$R^{3A}$ is $CH_3$, $CH(CH_3)_2$; $C(CH_3)_3$, $OCH_3$, OH, $OR^{3B}$, C≡CH, C≡N, unsubstituted phenyl or phenyl substituted by one, two or three substituents selected from $C_1$-$C_6$-alkyl, trifluoromethyl, $C_1$-$C_6$-alkoxy, $C_1$-$C_6$-alkylcarbonyl, $C_1$-$C_6$-alkylcarbonyloxy, $C_1$-$C_6$-alkylthio, nitro, amino, $C_1$-$C_6$-alkylamino, di-$C_1$-$C_6$-alkylamino, pyrrolidino, piperidino, morpholino, $C_1$-$C_6$-alkylcarbonylamino, and halogen;

unsubstituted 2- or 3-furanyl or 2- or 3-furanyl substituted by one or two substituents selected from $C_1$-$C_6$-alkyl, trifluoromethyl, $C_1$-$C_6$-alkoxy, and halogen; or unsubstituted 2- or 3-thienyl or 2- or 3-thienyl substituted by one or two substituents selected from $C_1$-$C_6$-alkyl, trifluoromethyl, $C_1$-$C_6$-alkoxy, and halogen; and wherein $R^{3B}$ is unsubstituted phenyl or phenyl substituted by one, two or three substituents selected from $C_1$-$C_6$-alkyl, trifluoromethyl, $C_1$-$C_6$-alkoxy, $C_1$-$C_6$-alkylcarbonyl, $C_1$-$C_6$-alkylcarbonyloxy, $C_1$-$C_6$-alkylthio, nitro, amino, $C_1$-$C_6$-alkylamino, di-$C_1$-$C_6$-alkylamino, pyrrolidino, piperidino, morpholino, $C_1$-$C_6$-alkylcarbonylamino, and halogen;

A is selected from partial structures a to i as defined above;

$X^1$ is O, NH, or N($CH_3$); and $X^2$ is O, S or NH.

More preferred compounds of formula 1 in the pharmaceutical compositions of the invention are those wherein $R^1$ is unsubstituted phenyl; unsubstituted 2-, 3- or 4-pyridyl; or unsubstituted indolyl;

$R^2$ is $(CH_2)_n$ wherein n is 0, 1 or 2;

$R^3$ is $(CH_2)_m R^{3A}$ wherein m is 0, 1, 2, 3 or 4;

$R^{3A}$ is $CH_3$, $CH(CH_3)_2$; $C(CH_3)_3$, $OCH_3$, OH, $OR^{3B}$, C≡CH, C≡N, unsubstituted phenyl or phenyl substituted by one, two or three substituents selected from $C_1$-$C_6$-alkyl, trifluoromethyl, $C_1$-$C_6$-alkoxy, and halogen;

unsubstituted 2- or 3-furanyl or unsubstituted 2- or 3-thienyl; and wherein $R^{3B}$ is unsubstituted phenyl or phenyl substituted by one, two or three substituents selected from $C_1$-$C_6$-alkyl, trifluoromethyl, $C_1$-$C_6$-alkoxy, and halogen;

A is selected from partial structures a to i as defined above;

$X^1$ is O, NH, or N($CH_3$); and $X^2$ is O.

Equally preferred are compounds of formula 1 in the pharmaceutical compositions of the invention wherein $R^1$ is unsubstituted phenyl; unsubstituted 2-, 3- or 4-pyridyl; or unsubstituted indolyl;

$R^2$ is $(CH_2)_n$ wherein n is 0, 1 or 2;

$R^3$ is $(CH_2)_m CH_3$, $(CH_2)_m$C≡CH or $(CH_2)_m$C≡N wherein m is 2 or 3;

A is selected from partial structures a to d and f to i as defined above;

$X^1$ is O, NH, or N($CH_3$); and $X^2$ is O.

Even more preferred are compounds of formula 1 in the pharmaceutical compositions of the invention wherein $R^1$ is phenyl or 2-, 3- or 4-pyridyl;

$R^2$ is $(CH_2)_n$ wherein n is 0, 1 or 2;

$R^3$ is $(CH_2)_m R^{3A}$ wherein m is 1, 2, 3 or 4;

$R^{3A}$ is $CH_3$; $CH(CH_3)_2$; $C(CH_3)_3$; $OCH_3$; $OR^{3B}$; unsubstituted phenyl or phenyl substituted by one or two substituents selected from $C_1$-$C_6$-alkyl, trifluoromethyl, $C_1$-$C_6$-alkoxy, and halogen; 2- or 3-furanyl; or 2- or 3-thienyl; and wherein $R^{3B}$ is unsubstituted phenyl or phenyl substituted by one or two substituents selected from $C_1$-$C_6$-alkyl, trifluoromethyl, $C_1$-$C_6$-alkoxy, and halogen;

A is selected from partial structures a to h as defined above;

$X^1$ is O or NH; and $X^2$ is O.

Particularly preferred are compounds of formula 1 in the pharmaceutical compositions of the invention wherein $R^1$ is phenyl or 2-, 3- or 4-pyridyl;

$R^2$ is $(CH_2)_n$ wherein n is 0, 1 or 2;

$R^3$ is $(CH_2)_m R^{3A}$ wherein m is 1, 2, 3 or 4;

$R^{3A}$ is $CH_3$; $CH(CH_3)_2$; $C(CH_3)_3$; $OCH_3$; $OR^{3B}$; phenyl; 2-furanyl; or 2-thienyl; and wherein $R^{3B}$ is unsubstituted phenyl or phenyl substituted by halogen;

A is selected from partial structures a, b, c, e, f, g, and h as defined above;

$X^1$ is O or NH; and $X^2$ is O.

Most preferred compounds of formula 1 in the pharmaceutical compositions of the invention are those of the Examples.

Preferred compounds of formula 2 in the pharmaceutical compositions of the invention are those wherein $R^4$ is optionally substituted pyridyl, $NR^7R^8$, or —NH—N═CH—$R^9$;

$R^5$ is hydrogen, optionally substituted phenyl, or a sugar residue;

$R^6$ is hydrogen;

$R^7$ is optionally substituted phenyl or a sugar residue;

$R^8$ is hydrogen; and $R^9$ is optionally substituted phenyl.

Even more preferred are compounds of formula 2 in the pharmaceutical compositions of the invention wherein $R^4$ is substituted pyridyl, $NR^7R^8$, or —NH—N═CH—$R^9$;

$R^5$ is hydrogen, substituted phenyl, or a sugar residue;

$R^6$ is hydrogen;

$R^7$ is substituted phenyl or a sugar residue;

$R^8$ is hydrogen; and $R^9$ is substituted phenyl.

Most preferred are compounds of formula 2 in the pharmaceutical compositions of the invention wherein $R^4$ is pyridyl substituted by $C_1$-$C_6$-alkyl, $NR^7R^8$, or —NH—N═CH—$R^9$;

$R^5$ is hydrogen, phenyl substituted by $C_1$-$C_6$-alkoxy, or a sugar residue;

$R^6$ is hydrogen;
$R^7$ is phenyl substituted by $C_1$-$C_6$-alkoxy, or a sugar residue;
$R^8$ is hydrogen; and
$R^9$ is phenyl substituted by $C_1$-$C_6$-alkylcarbonylamino.

Particularly preferred are compounds of formula 2 in the pharmaceutical compositions of the invention wherein $R^4$ is 4-pyridyl substituted by $C_1$-$C_6$-alkyl; $R^5$ is hydrogen or a sugar residue; and $R^6$ is hydrogen; in particular ethionamide of formula 8:

8 compounds of formula 2 wherein $R^4$ is —NH—N═CH—$R^9$; $R^5$ is hydrogen or a sugar residue; $R^6$ is hydrogen; and $R^9$ is phenyl substituted by $C_1$-$C_6$-alkylcarbonylamino, in particular thiacetazone of formula 9:

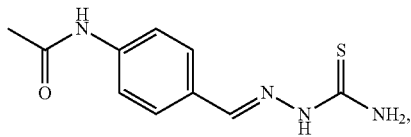

9 and
compounds of formula 2 wherein $R^4$ is —$NR^7R^8$; $R^5$ is phenyl substituted by $C_1$-$C_6$-alkoxy; $R^6$ is hydrogen; $R^7$ is phenyl substituted by $C_1$-$C_6$-alkoxy or a sugar residue; and $R^8$ is hydrogen; in particular isoxyl of formula 10:

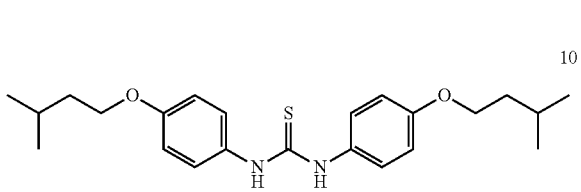 [SMILES: CC(C)CCOc1ccc(NC(=S)Nc2ccc(OCCC(C)C)cc2)cc1]

10 or the isoxyl analog N-arabinofuranosyl-N'-[p-(isoamyloxy)phenyl]-thiourea of formula 11:

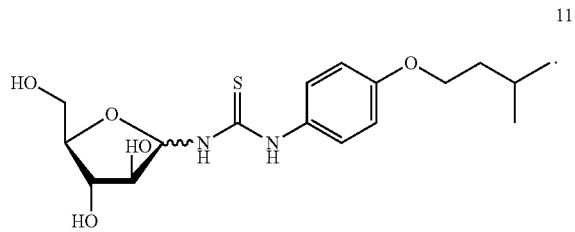

11

Most preferred is a composition comprising a compound of formula 1 and a compound of formula 2 selected from ethionamide, isoxyl, N-arabinofuranosyl-N'-[p-(isoamyloxy)phenyl]-thiourea or thiacetazone, in particular ethionamide.

It is understood that a pharmaceutical composition according to the invention comprising a compound of formula 1 as herein described and a compound of formula 2 as herein described may be a pharmaceutical composition comprising a mixture of a compound of formula 1 and a compound of formula 2, or two separate formulations of a compound of formula 1 and of a compound of formula 2, those two formulations being packaged together or provided separately.

Compounds of formula 1 are known or can be made according to methods well known in the art.

Compounds of formula 2 are known or can be manufactured as follows:

Thioamides, i.e. compounds of formula 2 wherein $R^4$ is optionally substituted phenyl, optionally substituted pyridyl or optionally substituted indolyl, are obtainable by reacting an amine of formula $HNR^5R^6$ with a carboxylic acid of formula $R^4$—COOH to form an amide of formula $R^4$—CO—$NR^5R^6$. The amide is reacted with Lawesson's reagent or phosphorus pentasulfide, to obtain the thioamide of formula 2. Another method to synthesize the thioamides is via the Kindler modification of the Willgerodt reaction using an aldehyde of formula $R^4$—CH═O and an amine of formula $HNR^5R^6$ and react them in the presence of sulphur.

Thioureas, i.e. compounds of formula 2 wherein $R^4$ is —$NR^7R^8$, are obtainable by reacting a bromide with potassium thiocyanate to give an isothiocyanate of formula $R^5$—N═C═S or $R^7$—N═C═S, which is reacted with an amine of formula $HNR^7R^8$ or $HNR^5R^6$, respectively. Corresponding hydrazones, i.e. compounds of formula 2 wherein $R^4$ is —NH—N═CH—$R^9$, are obtainable by reacting an aldehyde of formula $R^9$—CH═O with an hydrazinocarbothioamide of formula $R^5R^6N$—(C═S)—NH—$NH_2$.

The invention also relates to new compounds as such of formula 1 as defined hereinbefore.

In particular the invention relates to compounds of formula 1

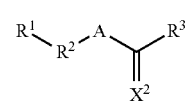

1 wherein
$R^1$ is phenyl or 2-pyridyl; $R^2$ is $(CH_2)_n$ wherein n is 0, 1 or 2; $R^3$ is $(CH_2)_m R^{3.A}$ wherein m is 1, 2 or 3; $R^{3.A}$ is $CH_3$ or phenyl;
A is

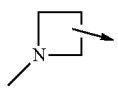

e wherein - represents the bond to C(═$X^2$)—$R^3$ and → represents the bond to $R^2$—$R^1$; or A together with —C(═$X^2$)—$R^3$ forms a ring

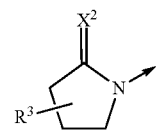

f

-continued

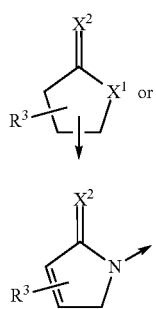

wherein → represents the bond to R²—R¹;
X¹ is O; and X² is O;
or wherein
R¹ is phenyl; R² is a bond; R³ is (CH₂)₄CH₃;
A is

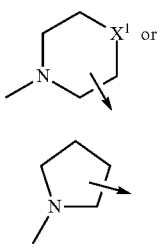

wherein - represents the bond to C(=X²)—R³ and → represents the bond to R²—R¹;
X¹ is O; and X² is O.

More particularly the invention relates to compounds of formula 1 wherein
R¹ is phenyl; R² is (CH₂)ₙ wherein n is 0 or 1;
R³ is (CH₂)ₘR³′⁴ wherein m is 1, 2 or 3, and R³′⁴ is CH₃ or phenyl;
A is

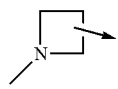

and
X² is O.

Likewise the invention relates to compounds of formula 1 wherein
R¹ is phenyl; R² is a bond; R³ is (CH₂)₄CH₃;
A is

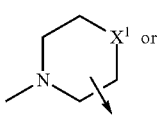

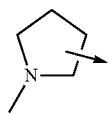

wherein - represents the bond to C(=X²)—R³ and → represents the bond to R²—R¹;
X¹ is O; and X² is O.

Most preferred are the compounds of Examples 2, 4 to 12, 22 to 27, 31 and 33.

The invention likewise relates to the use of a composition comprising a compound of formula 1 and of formula 2, e.g. ethionamide, in the treatment of tuberculosis and related diseases, and to a method of treatment of tuberculosis and related diseases wherein a composition comprising a compound of formula 1 and of formula 2, e.g. ethionamide, is applied.

The invention relates to a pharmaceutical composition comprising a compound of formula 1 as defined hereinbefore and a compound of formula 2 as defined hereinbefore, preferably ethionamide.

As a consequence of adding a compound of formula 1 preventing EthR from binding to the ethA promoter to a pharmaceutical composition useful in the treatment of tuberculosis, the dose of the thioamide or thiourea, i.e. the compound of formula 2, may be substantially reduced, reducing thereby the known side effects without reducing their efficacy.

The pharmaceutical compositions of the invention are not only useful for the treatment of tuberculosis, i.e. a disease caused by *Mycobacterium tuberculosis*, but also for the treatment of diseases caused by related bacteria with EthR related proteins binding to the corresponding ethA related promoter, in particular *Mycobacterium leprae*, *Mycobacterium ulcerans*, *Mycobacterium marinum*, *Mycobacterium* sp. MCS, *Mycobacterium* sp. KMS, *Mycobacterium* sp. JLS, *Mycobacterium vanbaalenii*, *Mycobacterium avium* subsp. *paratuberculosis*, *Mycobacterium avium*, *Mycobacterium smegmatis*, *Mycobacterium gilvum*, *Mycobacterium abscessus*, *Acinetobacter baumannii*, *Renibacterium salmoninarum*, *Mycobacterium gilvum*, *Streptococcus pyogenes*, *Bacillus licheniformis*, *Clostridium spiroforme*, and *Bacillus anthracis*. Such diseases are leprosy, buruli-ulcer disease, atypical mycobacteriosis, Johne's and Crohn's disease, hot tub lung, lady Windermere syndrome, chronic lung disease, post-traumatic wound infections, post-tympanostomy tube otorrhea, disseminated cutaneous diseases, *Acinetobacter baumanii* caused infections, pharyngitis, impetigo, erysipelas, cellulitis, necrotizing fasciitis, scarlet fever, toxic shock septicaemia, peritonitis, ophthalmitis, diarrhoea and splenic fever.

Pharmaceutical compositions according to the invention are compositions for enteral administration, such as nasal, buccal, rectal or, especially, oral administration, and for parenteral administration, such as intravenous, intramuscular or subcutaneous administration. The compositions comprise a compound of formula 1 and a compound of formula 2 preferably together with a pharmaceutically acceptable carrier. The dosage of the active ingredients depends upon the patient, its age, weight, and individual condition, the individual pharmacokinetic data, and the mode of administration.

The invention relates also to the described pharmaceutical compositions for use in a method for the prophylactic or especially therapeutic management of the human or animal body, in particular in a method of treating tuberculosis, leprosy, buruli-ulcer disease, atypical mycobacteriosis, Johne's and Crohn's disease, hot tub lung, lady Windermere syndrome, chronic lung disease, post-traumatic wound infections, post-tympanostomy tube otorrhea, disseminated cutaneous diseases, *Acinetobacter baumanii* caused infections, pharyngitis, impetigo, erysipelas, cellulitis, necrotizing fasciitis, scarlet fever, toxic shock septicaemia, peritonitis, ophthalmitis, diarrhoea and splenic fever.

The pharmaceutical compositions comprise from approximately 5% to approximately 95% of a mixture of a compound of formula 1 and of a compound of formula 2 in relative molar amounts of between 1:1 up to 1:10,000, preferably 1:10 up to 1:5000. Single-dose administration forms comprise from approximately 20% to approximately 90% of the mentioned mixture, and forms that are not of single-dose type from approximately 5% to approximately 20% of the mentioned mixture. Unit dose forms are, for example, coated and uncoated tablets, ampoules, vials, suppositories, or capsules. Further dosage forms are, for example, ointments, creams, pastes, foams, tinctures, lip-sticks, drops, syrups, sprays, and the like. Examples are capsules containing from about 0.05 g to about 1.0 g of a mixture of the active ingredients.

It is also possible to use the mixture of a compound of formula 1 and of a compound of formula 2 in two separate pharmaceutical unit dose forms, and such a combination is also part of the present invention. For example, a compound of formula 2, e.g. ethionamide, may be used in amounts of 0.01 g to about 0.5 g, e.g. in commercially available unit dose forms comprising from 0.05 g to about 0.5 g ethionamide, in combination with a different or same unit dose form comprising the compound of formula 1, in amounts of 0.5 g to about 5.0 g, as a kit of parts.

The pharmaceutical compositions of the present invention are prepared in a manner known per se, for example by means of conventional mixing, granulating, coating, dissolving, emulsifying or lyophilizing processes. Optionally, the compound of formula 1 can be formulated in liposomes.

For parenteral administration solutions of the active ingredients are preferred, and also suspensions, emulsions or dispersions, especially isotonic aqueous solutions, dispersions, emulsions or suspensions which, for example in the case of lyophilized compositions comprising the active ingredients alone or together with a carrier, for example mannitol, can be made up before use. The pharmaceutical compositions may be sterilized and/or may comprise excipients, for example preservatives, stabilizers, wetting agents and/or emulsifiers, solubilizers, salts for regulating osmotic pressure and/or buffers and are prepared in a manner known per se, for example by means of conventional dissolving and lyophilizing processes. The said solutions or suspensions may comprise viscosity-increasing agents, typically sodium carboxymethylcellulose, carboxymethyl-cellulose, dextran, polyvinylpyrrolidone, or gelatins, or also solubilizers, e.g. Tween 80® (polyoxyethylene(20)sorbitan mono-oleate).

Suspensions in oil comprise as the oil component the vegetable, synthetic, or semi-synthetic oils customary for injection purposes. In respect of such, special mention may be made of liquid fatty acid esters that contain as the acid component a long-chained fatty acid having from 8 to 22, especially from 12 to 22, carbon atoms. The alcohol component of these fatty acid esters has a maximum of 6 carbon atoms and is a monovalent or polyvalent, for example a mono-, di- or trivalent, alcohol, especially glycol and glycerol. As mixtures of fatty acid esters, vegetable oils such as cottonseed oil, almond oil, olive oil, castor oil, sesame oil, soybean oil and groundnut oil are especially useful.

The manufacture of injectable preparations is usually carried out under sterile conditions, as is the filling, for example, into ampoules or vials, and the sealing of the containers.

Suitable carriers for oral compositions are especially fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinyl-pyrrolidone, and/or, if desired, disintegrators, such as the above-mentioned starches, also carboxymethyl starch, crosslinked polyvinylpyrrolidone, alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Tablet cores can be provided with suitable, optionally enteric, coatings through the use of, inter alia, concentrated sugar solutions which may comprise gum arabic, talc, polyvinyl-pyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropyl-methylcellulose phthalate. Dyes or pigments may be added to the tablets or tablet coatings, for example for identification purposes or to indicate different doses of active ingredient.

Pharmaceutical compositions for oral administration also include hard capsules consisting of gelatin, and also soft, sealed capsules consisting of gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient is preferably dissolved, emulsified or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Pharmaceutical compositions suitable for rectal administration are, for example, suppositories that consist of a combination of the active ingredient and a suppository base. Suitable suppository bases are, for example, natural or synthetic triglycerides, paraffin hydrocarbons, polyethylene glycols or higher alkanols.

The present invention relates furthermore to a method for the treatment of tuberculosis and related diseases, which comprises administering a mixture of a compound of formula 1 and of a compound of formula 2, in a quantity effective against said disease, to a warm-blooded animal requiring such treatment. The mixture can be administered in the form of pharmaceutical compositions comprising the mixture, or also the components separately at the same time or at different times within the day, prophylactically or therapeutically, preferably in an amount effective against tuberculosis or the related disease, to a warm-blooded animal, for example a human, requiring such treatment. In the case of an individual having a bodyweight of about 70 kg the daily dose of the mixture administered is from approximately 0.01 g to approximately 50 g, preferably from approximately 0.05 g to approximately 10 g, of a mixture containing the components in relative amounts of between 1:1 and 1:10'000.

The present invention relates especially also to the use of a compound of formula 1, as such or in the form of a pharmaceutical formulation with at least one pharmaceutically acceptable carrier for the therapeutic and also prophylactic management of tuberculosis in combination with a compound of formula 2, such as ethionamide, administered either separately or in a fixed combination. The preferred dose quantity, composition, and preparation of pharmaceutical formulations which are to be used in each case are described above.

The following Examples serve to illustrate the invention without limiting the invention in its scope.

EXAMPLES

Vector Design pWW489 ($P_{SV40}$-ethR-vp16-pA) is constructed by PCR-mediated amplification of ethR from genomic *M. bovis* DNA using oligonucleotides OWW400 and OWW401 (Weber W. et al., PNAS 2008, 105, 9994-8) followed by restriction and ligation (EcoRI/BssHII) into pWW35 (Weber, W. et al., Nat Biotechnol 2002, 20, 901-7). pWW491 ($O_{ethR}$-$P_{hsp70min}$-SEAP-pA) is obtained by direct cloning of a synthetic $O_{ethR}$ sequence (Weber W. et al., PNAS 2008, 105, 9994-8) (AatII/SbfI) into pMF172 (Weber, W. et al., supra). pWW871 (5'LTR-$\Psi^+$-ethR-vp16-$P_{PGK}$-$neo^R$-3'LTR) was designed by cloning ethR-vp16 of pWW489 (EcoRI/BamHI) into pMSCVneo (Clontech).

Cell Culture

Human embryonic kidney cells (HEK-293, ATCC CRL-1573) are cultivated in Dulbecco's modified Eagle's medium (DMEM; Invitrogen, Carlsbad, Calif., USA) supplemented with 10% fetal calf serum (Pan Biotech GmbH, Aidenbach, Germany, cat. no. 3302, lot P231902) and 1% of a penicillin/streptomycin solution (Sigma, St. Louis, Mo., USA, cat. no. 4458). Cells are transfected using standard calcium phosphate procedures (Weber W. et al., supra) and retroviral particles are produced according to the manufacturer's protocol (Clontech). $_{EthR}$HEK, transgenic for constitutive EthR-VP16 expression, is constructed by transducing HEK-293 with pWW871-derived retroviral particles followed by selection in DMEM containing 200 μg/ml neomycin and single-cell cloning. Cotransfection of $_{EthR}$HEK with pWW491 and pPUR (Clontech), subsequent selection in 200 μg/ml neomycin, 1 μg/ml puromycin followed by single-cell cloning resulted in $_{EthR}$HEK-SEAP. SEAP production is quantified as described in Schlatter, S. et al., Gene 2002, 282, 19-31.

*Mycobacteria* Cultivation and Susceptability Testing Using the MGIT 960 System with EpiCenter TB eXiST Software

*M. tuberculosis* H37Rv (ATCC27294) is grown in Middlebrook 7H9 supplemented with oleic acid, albumin, dextrose, catalase (Difco) and Tween 80 (0.05%) until mid-log phase. For drug susceptibility testing, the MGIT 960 system (Becton Dickinson) was used according to the manufacturers' manual. 0.8 ml of MGIT 960 SIRE supplement (Becton Dickison) and 0.2 ml of the drug solution were added to the MGIT tubes. The tubes were inoculated with 0.5 ml of test strain suspension. As a control, a drug-free MGIT tube was inoculated with 0.5 ml of a 1:100 diluted (sterile $H_2O$) suspension of the test strain. Growth of the bacteria was monitored by the EpiCenter software (version 5.6.6), equipped with the TB eXiST module (Becton Dickinson) and was expressed as growth units (GU). A strain was considered to be resistant (R) to a drug when the test tube reached ≥100 GU earlier than the drug-free control tube reached a GU-value of 400. Sensitivity (S) of a strain was defined when the control tube reached 400 GU and the test tube remained ≤100 GU for more than 7 days after the control tube has reached 400 GU.

A strain was considered to be intermediate (I) when the test tube reached ≥100 GU within 7 days after the control tube reached 400 GU.

Liquid Chromatography (LC)

HPLC Column: Reverse Phase, Zorbax SB-C18 1.8 μm 4.6×15 mm Rapid Resolution cartridge; Wavelength: 210 nm to 400 nm; HPLC Apparatus Type: Agilent 1100, Photodiode array detector (PDA); MS Apparatus Type: Agilent SL, positive/negative mode switching, Ionization mode ESI.

LCMS System 01 (LCMS 01): Gradient 01

Solvent A: Acetonitrile/water (95:5), 0.1% formic acid; Solvent B: Water, 0.1% formic acid;

| Time (min) | Flow (mL/min) | % A | % B |
|---|---|---|---|
| 0.00 | 3 | 0 | 100 |
| 0.01 | 3 | 0 | 100 |
| 0.50 | 3 | 100 | 0 |
| 0.95 | 3 | 100 | 0 |
| 0.96 | 3 | 0 | 100 |
| 1.00 | 3 | 0 | 100 |

LCMS System $O_2$ (LCMS 02): Gradient $O_2$

Solvent A: Water, 0.1% formic acid; Solvent B: Methanol, 0.1% formic acid

| Time (min) | Flow (mL/min) | % A | % B |
|---|---|---|---|
| 0.00 | 3 | 100 | 0 |
| 0.02 | 3 | 100 | 0 |
| 1.50 | 3 | 0 | 100 |
| 2.30 | 3 | 0 | 100 |
| 2.4 | 3 | 100 | 0 |
| 2.5 | 3 | 100 | 0 |

Example 1

1-(4-Benzylpiperazin-1-yl)butan-1-one

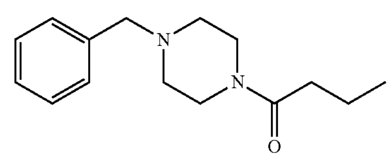 [SMILES: CCCC(=O)N1CCN(Cc2ccccc2)CC1]

A solution of 1-benzylpiperazine (352 mg, 2 mmol) in dry dichloromethane (6 mL) is cooled in an ice bath, and butanoyl chloride (266 mg, 2.5 mmol, 1.25 eq) and triethylamine (417 μL, 3 mmol, 1.5 eq) are added. After stirring for 6 hours at room temperature the reaction mixture is diluted with dichloromethane (10 mL). The organic solution is subsequently washed with 1 M $KHSO_4$, 5% $NaHCO_3$ and brine. After drying over $Na_2SO_4$, dichloromethane is removed in vacuo and the crude material is purified by flash chromatography (silicagel, ethyl acetate/toluene 1:1). The fractions containing 1-(4-benzylpiperazin-1-yl)butan-1-one are collected and the solvent is removed in vacuo to give 432 mg of colorless oil.

LCMS ESI$^+$: 247.0 $(M+H)^+$, $R_t$=0.511 min (LCMS 01)

Example 2

1-(4-(Pyridin-2-ylmethyl)piperazin-1-yl)butan-1-one

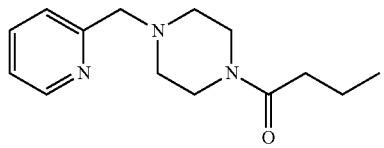 [SMILES: CCCC(=O)N1CCN(Cc2ccccn2)CC1]

To a solution of 1 eq 1-Boc-piperazine and 3 eq triethylamine in tetrahydrofuran (THF), 1 eq (2-bromomethyl)pyridine hydrobromide in tetrahydrofuran is added dropwise. After stirring overnight at room temperature, the reaction mixture is concentrated in vacuo to remove tetrahydrofuran and re-suspended in diethyl ether. The solution is filtered to remove triethylamine hydrobromide salt. The residue is washed with diethyl ether and the filtrate is concentrated in vacuo. The crude product is purified by column chromatography.

1-Boc-4-(pyridin-2-ylmethyl)piperazine is dissolved in diethyl ether and treated with saturated HCl/diethyl ether to remove the Boc-group. After stirring for 1 hour the solvents are removed in vacuo, resulting in 1-(pyridin-2-ylmethyl)piperazine hydrochloride.

To a solution of 1 eq 1-(pyridin-2-ylmethyl)piperazine hydrochloride in dry dichloromethane are added 1.5 eq butanoyl chloride and 2.5 eq triethylamine. After stirring for 6 hours at room temperature the solvent is removed in vacuo and the residue re-dissolved in ethyl acetate. The organic solution is subsequently washed with 1 M $KHSO_4$, 5% $NaHCO_3$ and brine. After drying over $Na_2SO_4$, ethyl acetate is removed in vacuo and the crude product is purified by column chromatography.

Example 3

1-(2-Phenylmorpholino)butan-1-one

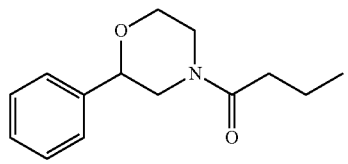 [SMILES: CCCC(=O)N1CCOC(c2ccccc2)C1]

A solution of 2-phenylmorpholine (326 mg, 2 mmol) in dry dichloromethane (6 mL) is cooled in an ice bath, and butanoyl chloride (266 mg, 2.5 mmol, 1.25 eq) and triethylamine (417 µL, 3 mmol, 1.5 eq) are added. After stirring for 6 hours at room temperature the reaction mixture is diluted with dichloromethane (10 mL). The organic solution is subsequently washed with 1 M $KHSO_4$, 5% $NaHCO_3$ and brine. After drying over $Na_2SO_4$, dichloromethane is removed in vacuo and the crude material is purified by flash chromatography (silicagel, ethyl acetate/toluene 1:3). The fractions containing 1-(2-phenylmorpholin-4-yl)butan-1-one are collected and the solvent is removed in vacuo to give 378 mg of colorless oil.

$^1$H-NMR ($D_6$-DMSO/$CCl_4$, 400 MHz) δ: 7.38 (m, 5 H), 4.37 (m, 2H), 4.00 (m, 1 H), 3.85 (m, 1 H), 3.55 (m, 1 H), 3.14 (m, 1 H), 2.66 (m, 1 H), 1.86 (m, 2 H), 1.54 (m, 2 H), 0.92 (t, 3 H).

Example 4

1-(2-(Pyridin-4-yl)morpholino)butan-1-one

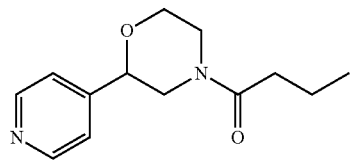 [SMILES: CCCC(=O)N1CCOC(c2ccncc2)C1]

To a solution of 1 eq 2-amino-1-(pyridin-3-yl)ethanol and 3 eq triethylamine in tetrahydro-furan, 1 eq of 2-bromoethanol is added dropwise. After stirring overnight at room temperature, the reaction mixture is concentrated in vacuo to remove tetrahydrofuran and re-suspended in diethyl ether. The solution is filtered to remove triethylamine hydrobromide salt. The residue is washed with diethyl ether and the filtrate is concentrated in vacuo. The crude 2-(2-hydroxyethylamino)-1-(pyridin-4-yl)ethanol is purified by crystallization.

2-(Pyridin-4-yl)morpholine is prepared by treating 2-(2-hydroxyethylamino)-1-(pyridin-4-yl)ethanol with fuming sulfuric acid at 170° C. according to F. Zymalkowski and F. Koppe (Arch. Pharmaz. 1961, 294, 453-468).

To a solution of 2-(pyridin-4-yl)morpholine in dry dichloromethane are added 1.5 eq butanoyl chloride and 2.5 eq triethylamine. After stirring for 6 hours at room temperature the solvent is removed in vacuo and the residue redisolved in ethyl acetate. The organic solution is subsequently washed with 1 M $KHSO_4$, 5% $NaHCO_3$ and brine. After drying over $Na_2SO_4$, ethyl acetate is removed in vacuo and the crude 1-(2-(pyridin-4-yl)morpholino)butan-1-one is purified by column chromatography.

Example 5

1-Phenethyl-3-propylpyrrolidin-2-one

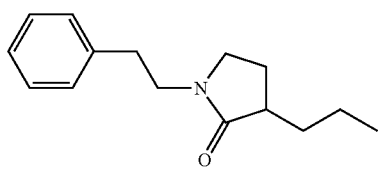 [SMILES: CCCC1CCN(CCc2ccccc2)C1=O]

1-Phenylethyl-2-pyrrolidone is prepared from 2-pyrrolidone and 2-bromoethylbenzene in N,N-dimethylformamide in the presence of sodium hydride (M. Matsukawa et al. NeuroToxicology 2004, 25, 293-302).

To a 2 M lithium diisopropylamine solution in tetrahydrofuran of −78° C. is added 1-phenylethyl-2-pyrrolidone and the mixture is stirred for 1.5 h at −78° C. Then 1-propyl bromide is added and the reaction is stirred for another 1.5 h at −78° C. The reaction mixture is allowed to warm up to 0° C. before ice-cold water with acetic acid is added and subsequently extracted 3 times with dichloromethane. The dichloromethane is concentrated in vacuo and the residue is dissolved in dichloromethane, washed with saturated NaHCO₃ and brine. Crude 1-phenethyl-3-propylpyrrolidin-2-one is obtained after removal of the solvents in vacuo. The product is purified by column chromatography.

Example 6

3-Propyl-1-(2-(pyridin-2-yl)ethyl)pyrrolidin-2-one

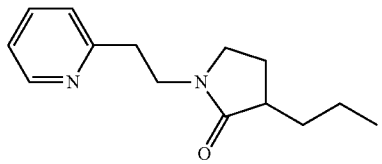 [SMILES: CCCC1CCN(CCc2ccccn2)C1=O]

1-(2-(Pyridin-2-yl)ethyl)pyrrolidin-2-one is prepared from 2-pyrrolidone and 2-bromo-ethylbenzene in N,N-dimethylformamide in the presence of sodium hydride (according to M. Matsukawa et al., NeuroToxicology 2004, 25, 293-302).

To a 2 M lithium diisopropylamine solution in THF of −78° C. is added 1-(2-(pyridin-2-yl)-ethyl)pyrrolidin-2-one and the mixture is stirred for 1.5 h at −78° C. Then 1-propyl bromide is added and the reaction is stirred for another 1.5 h at −78° C. The reaction mixture is allowed to warm up to 0° C. before ice-cold water with acetic acid is added and subsequently extracted 3 times with dichloromethane. The dichloromethane is concentrated in vacuo and the residue is dissolved in dichloromethane, washed with saturated NaHCO₃ and brine. Crude 3-propyl-1-(2-(pyridin-2-yl)ethyl)pyrrolidin-2-one is obtained after removal of the solvents in vacuo. The product is purified by column chromatography.

Example 7

5-Benzyl-3-propylpyrrolidin-2-one

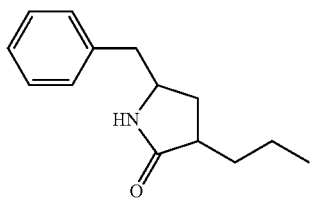

5-Benzylpyrrolidin-2-one is synthesized from pyrrolidine-2,5-dione and benzyl bromide according to S. Lebrun et al. (Tetrahedron Asymmetry 2003, 14, 2625-2632).

To a 2 M lithium diisopropylamine solution in THF of −78° C. is added 5-benzylpyrrolidin-2-one and the mixture is stirred for 1.5 hours at −78° C. Then 1-propyl bromide is added and the reaction is stirred for another 1.5 hours at −78° C. The reaction mixture is allowed to warm up to 0° C. before ice-cold water with acetic acid is added and subsequently extracted 3 times with dichloromethane. The dichloromethane is concentrated in vacuo and the residue is dissolved in dichloromethane, washed with saturated NaHCO₃ and brine. Crude 5-benzyl-3-propylpyrrolidin-2-one is obtained after removal of the solvents in vacuo. The product is purified by column chromatography.

Example 8

3-Propyl-5-(pyridin-2-ylmethyl)pyrrolidin-2-one

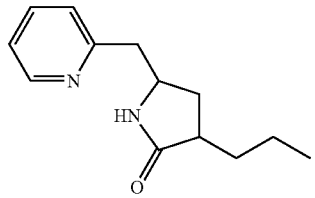 [SMILES: CCCC1CC(Cc2ccccn2)NC1=O]

5-(Pyridin-2-ylmethyl)pyrrolidin-2-one is synthesized from pyrrolidine-2,5-dione and 2-(bromomethyl)pyridine according to S. Lebrun et al. (Tetrahedron Asymmetry 2003, 14, 2625-2632).

To a 2 M lithium diisopropylamine solution in THF of −78° C. is added 5-(pyridin-2-ylmethyl)pyrrolidin-2-one, and the mixture is stirred for 1.5 hours at −78° C. Then 1-propyl bromide is added and the reaction is stirred for another 1.5 hours at −78° C. The reaction mixture is allowed to warm up to 0° C. before ice-cold water with acetic acid is added and subsequently extracted 3 times with dichloromethane. The dichloromethane is concentrated in vacuo and the residue is dissolved in dichloromethane, washed with saturated NaHCO₃ and brine. Crude 3-propyl-5-(pyridin-2-ylmethyl)pyrrolidin-2-one is obtained after removal of the solvents in vacuo. The product is purified by column chromatography.

Example 9

4-Ethyl-1-phenethyl-1H-pyrrol-2(5H)-one

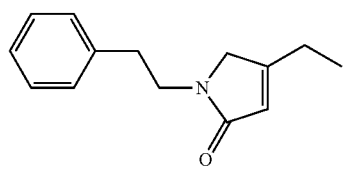 [SMILES: CCC1=CC(=O)N(CCc2ccccc2)C1]

4-Ethyl-1-phenethyl-1H-pyrrol-2(5H)-one is synthesized by a cyclocondensation between methyl 3-formylpentanoate and 2-phenylethylamine in glacial acetic acid at 70° C. according to a procedure of R. Fisher (DE 4127111, 1992)

Example 10

4-Ethyl-1-(2-(pyridin-2-yl)ethyl)-1H-pyrrol-2(5H)-one

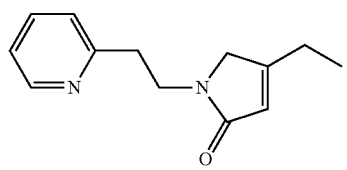 [SMILES: CCC1=CC(=O)N(CCc2ccccn2)C1]

4-Ethyl-1-(2-(pyridin-2-yl)ethyl)-1H-pyrrol-2(5H)-one is synthesized by a cyclo-condensation between methyl 3-formylpentanoate and 2-(pyridin-2-yl)ethanamine in glacial acetic acid at 70° C. according to a procedure of R. Fisher (DE 4127111, 1992).

Example 11

5-Benzyl-3-propyldihydrofuran-2(3H)-one

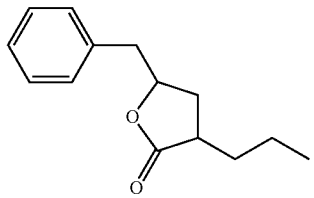 [SMILES: CCCC1CC(Cc2ccccc2)OC1=O]

Starting from the amino acid valine and 2-phenylacetic acid, 4-oxo-5-phenylpentanoic acid is prepared as described by W. Steglich and P. Gruber (Angew. Chem., 1971, 83, 727-728).

4-Oxo-5-phenylpentanoic acid is reduced with NaBH$_4$ and subsequently treated with hydrogen chloride to result in 5-benzylpyrrolidin-2-one (C. Ketterer et al., Tetrahedron Asymmetry 2006, 17, 3046-3050).

To a 2 M lithium diisopropylamine solution in THF of −78° C. is added 5-benzylpyrrolidin-2-one and the mixture is stirred for 1.5 hours at −78° C. Then 1-propyl bromide is added and the reaction is stirred for another 1.5 hours at −78° C. The reaction mixture is allowed to warm up to 0° C. before ice-cold water with acetic acid is added and subsequently extracted 3 times with dichloromethane. The dichloromethane is concentrated in vacuo and the residue is dissolved in dichloromethane, washed with saturated NaHCO$_3$ and brine. Crude 5-benzyl-3-propyldihydrofuran-2(3H)-one is obtained after removal of the solvents in vacuo. The product is purified by column chromatography.

Example 12

3-Propyl-5-(pyridin-2-ylmethyl)dihydrofuran-2(3H)-one

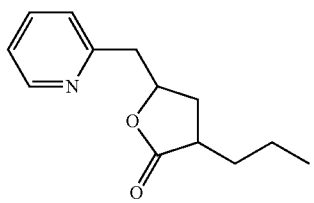 [SMILES: CCCC1CC(Cc2ccccn2)OC1=O]

According to the method of W. Steglich and P. Gruber (Angew. Chem., 1971, 83, 727-728), 4-oxo-5-(pyridin-2-yl)pentanoic acid is synthesized from valine and 2-(pyridin-2-yl)-acetic acid.

The reduction of 4-oxo-5-(pyridin-2-yl)pentanoic acid with NaBH$_4$ followed by a treatment with hydrogen chloride results in 5-(pyridin-2-ylmethyl)dihydrofuran-2(3H)-one (adapted from C. Ketterer et al., Tetrahedron Asymmetry 2006, 17, 3046-3050).

To a 2 M lithium diisopropylamine solution in THF of −78° C. is added 5-(pyridin-2-yl-methyl)dihydrofuran-2(3H)-one and the mixture is stirred for 1.5 hours at −78° C. Then 1-propyl bromide is added and the reaction is stirred for another 1.5 hours at −78° C. The reaction mixture is allowed to warm up to 0° C. before ice-cold water with acetic acid is added and subsequently extracted with 3 times dichloromethane. The dichloromethane is concentrated in vacuo and the residue is dissolved in dichloromethane, washed with saturated NaHCO$_3$ and brine. Crude 3-propyl-5-(pyridin-2-ylmethyl)dihydrofuran-2(3H)-one is obtained after removal of the solvents in vacuo. The product is purified by column chromatography.

Example 13

1-(3-Phenylpyrrolidin-1-yl)butan-1-one

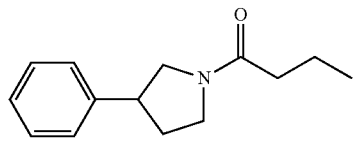 [SMILES: CCCC(=O)N1CCC(c2ccccc2)C1]

A solution of 3-phenylpyrrolidine (294 mg, 2 mmol) in dry dichloromethane (6 mL) is cooled in an ice bath, and butanoyl chloride (266 mg, 2.5 mmol, 1.25 eq) and triethylamine (417 µL, 3 mmol, 1.5 eq) are added. After stirring for 6 hours at room temperature the reaction mixture is diluted with dichloromethane (10 mL). The organic solution is subsequently washed with 1 M KHSO$_4$, 5% NaHCO$_3$ and brine. After drying over Na$_2$SO$_4$, dichloromethane is removed in vacuo and the crude material is purified by flash chromatography (silicagel, ethyl acetate/toluene 1:4). The fractions containing 1-(3-phenylpyrrolidin-1-yl)butan-1-one are collected and the solvent is removed in vacuo to give 378 mg of colorless oil.

$^1$H-NMR (D$_6$-DMSO/CCl$_4$, 400 MHz) δ: 7.25 (m, 5 H), 3.87 (m, 1 H), 3.65 (m, 1 H), 3.35 (m, 3 H), 2.20 (m, 3 H), 2.00 (m, 1 H), 1.60 (m, 2 H), 0.97 (t, 3 H).

LCMS ESI$^+$: 218.2 (M+H)$^+$, R$_t$=1.086 min (LCMS 02)

Example 14

1-(2-Phenylmorpholin-4-yl)-2-(thiophen-2-yl)ethan-1-one

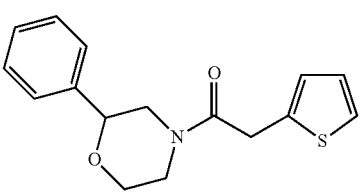 [SMILES: O=C(Cc1cccs1)N1CCOC(c2ccccc2)C1]

A solution of 2-phenylmorpholine (326 mg, 2 mmol) in dry dichloromethane (6 mL) is cooled in an ice bath, and thiophen-2-yl-acetyl chloride (401.5 mg, 2.5 mmol, 1.25 eq) and triethylamine (417 µL, 3 mmol, 1.5 eq) are added. After stirring for 6 hours at room temperature the reaction mixture is diluted with dichloromethane (10 mL). The organic solution is subsequently washed with 1 M KHSO$_4$, 5% NaHCO$_3$ and brine. After drying over Na$_2$SO$_4$, dichloromethane is removed in vacuo and the crude material is purified by flash chromatography (silicagel, ethyl acetate/toluene 1:3). The fractions containing 1-(2-phenylmorpholin-4-yl)-2-(thiophen-2-yl)ethan-1-one are collected and the solvent is removed in vacuo to give 511 mg of colorless oil.

LCMS ESI$^+$: 288.2 (M+H)$^+$, R$_t$=1.546 min (LCMS 02)

Example 15

2-(4-Fluorophenoxy)-1-(3-phenylpyrrolidin-1-yl)ethan-1-one

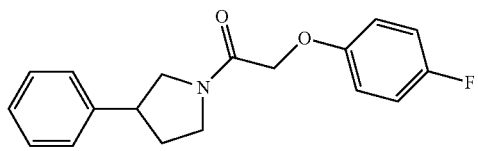 [SMILES: O=C(COc1ccc(F)cc1)N1CCC(c2ccccc2)C1]

A solution of 3-phenylpyrrolidine (294 mg, 2 mmol) in dry dichloromethane (6 mL) is cooled in an ice bath, and (4-fluoro-phenoxy)-acetyl chloride (471.5 mg, 2.5 mmol, 1.25 eq) and triethylamine (417 μL, 3 mmol, 1.5 eq) are added. After stirring for 6 hours at room temperature the reaction mixture is diluted with dichloromethane (10 mL). The organic solution is subsequently washed with 1 M KHSO$_4$, 5% NaHCO$_3$ and brine. After drying over Na$_2$SO$_4$, dichloromethane is removed in vacuo and the crude material is purified by flash chromatography (silicagel, ethyl acetate/toluene 1:4). The fractions containing 2-(4-fluorophenoxy)-1-(3-phenylpyrrolidin-1-yl)ethan-1-one are collected and the solvent is removed in vacuo to give 495 mg of colorless oil.

$^1$H-NMR (D$_6$-DMSO, 300 MHz) δ: 7.30 (m, 5 H), 6.94 (m, 4 H), 4.63 (m, 2H), 3.95 (m, 1 H), 3.68 (m, 2H), 3.40 (m, 2H), 2.31 (m, 1 H), 2.03 (m, 1 H).

Example 16

3-Phenyl-1-(3-phenylpyrrolidin-1-yl)propan-1-one

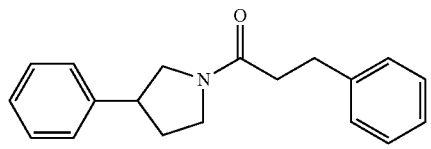 [SMILES: O=C(CCc1ccccc1)N1CCC(c2ccccc2)C1]

A solution of 3-phenylpyrrolidine (294 mg, 2 mmol) in dry dichloromethane (6 mL) is cooled in an ice bath, and 3-phenyl-propionyl chloride (421.5 mg, 2.5 mmol, 1.25 eq) and triethylamine (417 μL, 3 mmol, 1.5 eq) are added. After stirring for 6 hours at room temperature the reaction mixture is diluted with dichloromethane (10 mL). The organic solution is subsequently washed with 1 M KHSO$_4$, 5% NaHCO$_3$ and brine. After drying over Na$_2$SO$_4$, dichloromethane is removed in vacuo and the crude material is purified by flash chromatography (silicagel, ethyl acetate/toluene 1:5). The fractions containing 3-phenyl-1-(3-phenylpyrrolidin-1-yl)propan-1-one are collected and the solvent is removed in vacuo to give 521 mg of colorless oil.

$^1$H-NMR (D$_6$-DMSO/CCl$_4$, 300 MHz) δ: 7.15 (m, 10 H), 3.85 (m, 1 H), 3.62 (m, 1 H), 3.45 (m, 3H), 2.82 (m, 2 H), 2.55 (m, 2 H), 2.28 (m, 1H), 1.94 (m, 1 H).

Example 17

2-Phenyl-1-(3-phenylpyrrolidin-1-yl)ethan-1-one

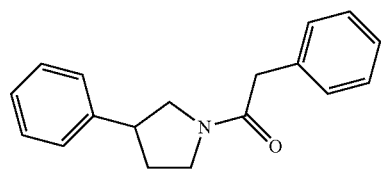 [SMILES: O=C(Cc1ccccc1)N1CCC(c2ccccc2)C1]

A solution of 3-phenylpyrrolidine (294 mg, 2 mmol) in dry dichloromethane (6 mL) is cooled in an ice bath, and phenylacetyl chloride (386.5 mg, 2.5 mmol, 1.25 eq) and triethylamine (417 μL, 3 mmol, 1.5 eq) are added. After stirring for 6 hours at room temperature the reaction mixture is diluted with dichloromethane (10 mL). The organic solution is subsequently washed with 1 M KHSO$_4$, 5% NaHCO$_3$ and brine. After drying over Na$_2$SO$_4$, dichloromethane is removed in vacuo and the crude material is purified by flash chromatography (silicagel, ethyl acetate/toluene 1:5). The fractions containing the 2-phenyl-1-(3-phenylpyrrolidin-1-yl)ethan-1-one are collected and the solvent is removed in vacuo to give 465 mg of colorless oil.

$^1$H-NMR (D$_6$-DMSO/CCl$_4$, 300 MHz) δ: 7.12 (m, 10 H), 3.96 (m, 1 H), 3.61 (m, 3 H), 3.38 (m, 3H), 2.39 (m, 1H), 2.01 (m, 1 H).

Example 18

1-(4-Benzylpiperazin-1-yl)-3-(furan-2-yl)propan-1-one

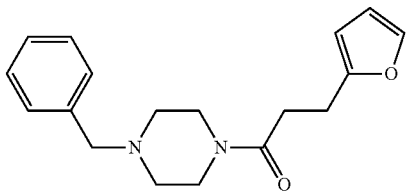 [SMILES: O=C(CCc1ccco1)N1CCN(Cc2ccccc2)CC1]

A solution of 1-benzylpiperazine (352 mg, 2 mmol) in dry dichloromethane (6 mL) is cooled in an ice bath, and 3-(furan-2-yl)propionyl chloride (396.5 mg, 2.5 mmol, 1.25 eq) and triethylamine (417 μL, 3 mmol, 1.5 eq) are added. After stirring for 6 hours at room temperature the reaction mixture is diluted with dichloromethane (10 mL). The organic solution is subsequently washed with 1 M KHSO$_4$, 5% NaHCO$_3$ and brine. After drying over Na$_2$SO$_4$, dichloromethane is removed in vacuo and the crude material is purified by flash chromatography (silicagel, ethyl acetate/toluene 1:2). The fractions containing the 1-(4-benzylpiperazin-1-yl)-3-(furan-2-yl)propan-1-one are collected and the solvent is removed in vacuo to give 497 mg of colorless oil.

LCMS ESI$^+$: 299.2 (M+H)$^+$, R$_t$=0.361 min (LCMS 01)

¹H-NMR (D₆-DMSO/CCl₄, 400 MHz) δ: 7.35 (s, 1 H), 7.27 (s, 4 H), 7.21 (s, 1H), 6.26 (s, 1 H), 6.02 (s, 1H), 3.45 (m, 6H), 2.83 (m, 2 H), 2.59 (m, 2 H), 2.34 (s, 4 H).

Example 19

3-Methyl-1-(2-phenylmorpholin-4-yl)butan-1-one

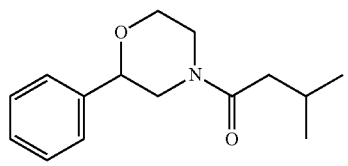 [SMILES: CC(C)CC(=O)N1CCOC(c2ccccc2)C1]

A solution of 2-phenylmorpholine (326 mg, 2 mmol) in dry dichloromethane (6 mL) is cooled in an ice bath, and 3-methyl-butyryl chloride (301.5 mg, 2.5 mmol, 1.25 eq) and triethylamine (417 μL, 3 mmol, 1.5 eq) are added. After stirring for 6 hours at room temperature the reaction mixture is diluted with dichloromethane (10 mL). The organic solution is subsequently washed with 1 M KHSO₄, 5% NaHCO₃ and brine. After drying over Na₂SO₄, dichloromethane is removed in vacuo and the crude material is purified by flash chromatography (silicagel, ethyl acetate/toluene 1:3). The fractions containing 3-methyl-1-(2-phenylmorpholin-4-yl)butan-1-one are collected and the solvent is removed in vacuo to give 465 mg of colorless oil.

¹H-NMR (CDCl₃, 400 MHz) δ: 7.43 (m, 5 H), 4.56 (m, 1 H), 4.36 (m, 1 H), 4.03 (m, 1 H), 3.74 (m, 1 H), 3.63 (m, 1 H), 3.20 (m, 1 H), 2.74 (m, 1 H), 2.18 (m, 3 H), 0.95 (m, 6 H).

Example 20

3,3-Dimethyl-1-(2-phenylmorpholin-4-yl)butan-1-one

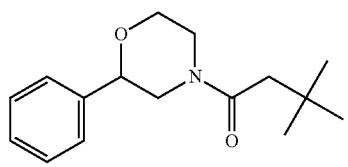 [SMILES: CC(C)(C)CC(=O)N1CCOC(c2ccccc2)C1]

A solution of 2-phenylmorpholine (326 mg, 2 mmol) in dry dichloromethane (6 mL) is cooled in an ice bath, and 3,3-dimethyl-butyryl chloride (336.5 mg, 2.5 mmol, 1.25 eq) and triethylamine (417 μL, 3 mmol, 1.5 eq) are added. After stirring for 6 hours at room temperature the reaction mixture is diluted with dichloromethane (10 mL). The organic solution is subsequently washed with 1 M KHSO₄, 5% NaHCO₃ and brine. After drying over Na₂SO₄, dichloromethane is removed in vacuo and the crude material is purified by flash chromatography (silicagel, ethyl acetate/toluene 1:4). The fractions containing the 3,3-dimethyl-1-(2-phenylmorpholin-4-yl)butan-1-one are collected and the solvent is removed in vacuo to give 438 mg of colorless oil.

¹H-NMR (CDCl₃, 400 MHz) δ: 7.34 (m, 5 H), 4.60 (m, 1 H), 4.35 (m, 1 H), 4.03 (m, 1 H), 3.80 (m, 1 H), 3.61 (m, 1 H), 3.18 (m, 1 H), 2.71 (m, 1 H), 2.24 (m, 2 H), 1.03 (s, 9 H).

Example 21

3-Phenyl-1-(2-phenylmorpholin-4-yl)propan-1-one

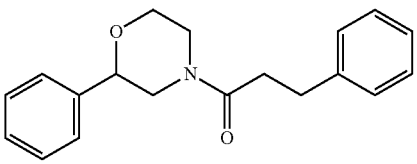 [SMILES: O=C(CCc1ccccc1)N1CCOC(c2ccccc2)C1]

A solution of 2-phenylmorpholine (326 mg, 2 mmol) in dry dichloromethane (6 mL) is cooled in an ice bath, and 3-phenylpropionyl chloride (421.5 mg, 2.5 mmol, 1.25 eq) and triethylamine (417 μL, 3 mmol, 1.5 eq) are added. After stirring for 6 hours at room temperature the reaction mixture is diluted with dichloromethane (10 mL). The organic solution is subsequently washed with 1 M KHSO₄, 5% NaHCO₃ and brine. After drying over Na₂SO₄, dichloromethane is removed in vacuo and the crude material is purified by flash chromatography (silicagel, ethyl acetate/toluene 1:4). The fractions containing 3-phenyl-1-(2-phenylmorpholin-4-yl)propan-1-one are collected and the solvent is removed in vacuo to give 528 mg of colorless oil.

¹H-NMR (D₆-DMSO, 400 MHz) δ: 7.36 (m, 5 H), 7.25 (m, 4 H), 7.17 (m, 1 H), 4.33 (m, 1 H), 4.30 (m, 1 H), 3.94 (m, 1 H), 3.81 (m, 1 H), 3.47 (m, 1 H), 3.11 (m, 1 H), 2.67 (m, 5 H).

Example 22

3-Phenyl-1-(2-phenylazetidin-1-yl)propan-1-one

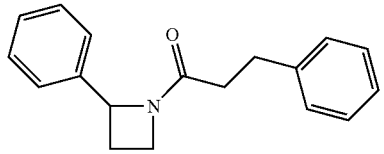 [SMILES: O=C(CCc1ccccc1)N1CCC1c1ccccc1]

A solution of 2-phenylazetidine (266 mg, 2 mmol) in dry dichloromethane (6 mL) is cooled in an ice bath, and 3-phenylpropionyl chloride (421.5 mg, 2.5 mmol, 1.25 eq) and triethylamine (417 μL, 3 mmol, 1.5 eq) are added. After stirring for 6 hours at room temperature the reaction mixture is diluted with dichloromethane (10 mL). The organic solution is subsequently washed with 1 M KHSO₄, 5% NaHCO₃ and brine. After drying over Na₂SO₄, dichloromethane is removed in vacuo and the crude material is purified by flash chromatography (silicagel, ethyl acetate/toluene 1:4). The fractions containing 3-phenyl-1-(2-phenylazetidin-1-yl)propan-1-one are collected and the solvent is removed in vacuo to give 397 mg of colorless oil.

LCMS ESI⁺: 266.0 (M+H)⁺, R$_t$=1.193 min (LCMS 02).

Example 23

4-Phenyl-1-(2-phenylazetidin-1-yl)butan-1-one

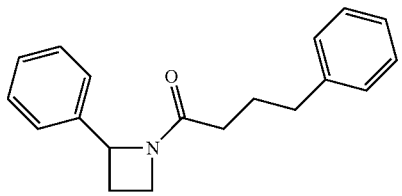 [SMILES: O=C(CCCc1ccccc1)N1CCC1c1ccccc1]

A solution of 2-phenylazetidine (266 mg, 2 mmol) in dry dichloromethane (6 mL) is cooled in an ice bath, and 4-phenylbutyryl chloride (456.6 mg, 2.5 mmol, 1.25 eq) and triethylamine (417 µL, 3 mmol, 1.5 eq) are added. After stirring for 6 hours at room temperature the reaction mixture is diluted with dichloromethane (10 mL). The organic solution is subsequently washed with 1 M KHSO$_4$, 5% NaHCO$_3$ and brine. After drying over Na$_2$SO$_4$, dichloromethane is removed in vacuo and the crude material is purified by flash chromatography (silicagel, ethyl acetate/toluene 1:5). The fractions containing 4-phenyl-1-(2-phenylazetidin-1-yl)butan-1-one are collected and the solvent is removed in vacuo to give 488 mg of colorless oil.

LCMS ESI$^+$: 280.2 (M+H)$^+$, R$_t$=1.239 min (LCMS 02).

Example 24

3-Phenyl-1-(3-phenylazetidin-1-yl)propan-1-one

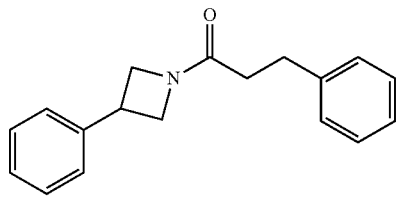 [SMILES: O=C(CCc1ccccc1)N1CC(c2ccccc2)C1]

A solution of 3-phenylazetidine (266 mg, 2 mmol) in dry dichloromethane (6 mL) is cooled in an ice bath, and 3-phenylpropionyl chloride (421.5 mg, 2.5 mmol, 1.25 eq) and triethylamine (417 µL, 3 mmol, 1.5 eq) are added. After stirring for 6 hours at room temperature the reaction mixture is diluted with dichloromethane (10 mL). The organic solution is subsequently washed with 1 M KHSO$_4$, 5% NaHCO$_3$ and brine. After drying over Na$_2$SO$_4$, dichloromethane is removed in vacuo and the crude material is purified by flash chromatography (silicagel, ethyl acetate/toluene 1:4). The fractions containing 3-phenyl-1-(3-phenylazetidin-1-yl)propan-1-one are collected and the solvent is removed in vacuo to give 421 mg of colorless oil.

Example 25

1-(3-Benzylazetidin-1-yl)-3-phenylpropan-1-one

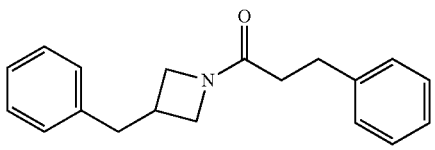 [SMILES: O=C(CCc1ccccc1)N1CC(Cc2ccccc2)C1]

A solution of 3-benzylazetidine (294 mg, 2 mmol) in dry dichloromethane (6 mL) is cooled in an ice bath, and 3-phenylpropionyl chloride (421.5 mg, 2.5 mmol, 1.25 eq) and triethylamine (417 µL, 3 mmol, 1.5 eq) are added. After stirring for 6 hours at room temperature the reaction mixture is diluted with dichloromethane (10 mL). The organic solution is subsequently washed with 1 M KHSO$_4$, 5% NaHCO$_3$ and brine. After drying over Na$_2$SO$_4$, dichloromethane is removed in vacuo and the crude material is purified by flash chromatography (silicagel, ethyl acetate/toluene 1:5). The fractions containing the ethyl 1-(3-benzylazetidin-1-yl)-3-phenylpropan-1-one are collected and the solvent is removed in vacuo to give 432 mg of colorless oil.

LCMS ESI$^+$: 280.0 (M+H)$^+$, R$_t$=1.216 min (LCMS 02).

Example 26

4-Phenyl-1-(3-phenylazetidin-1-yl)butan-1-one

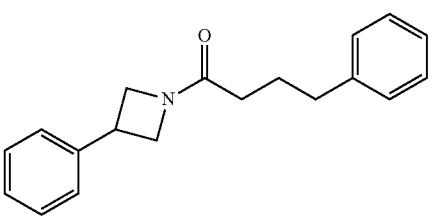 [SMILES: O=C(CCCc1ccccc1)N1CC(c2ccccc2)C1]

A solution of 3-phenylazetidine (266 mg, 2 mmol) in dry dichloromethane (6 mL) is cooled in an ice bath, and 4-phenylbutyryl chloride (456.6 mg, 2.5 mmol, 1.25 eq) and triethylamine (417 µL, 3 mmol, 1.5 eq) are added. After stirring for 6 hours at room temperature the reaction mixture is diluted with dichloromethane (10 mL). The organic solution is subsequently washed with 1 M KHSO$_4$, 5% NaHCO$_3$ and brine. After drying over Na$_2$SO$_4$, dichloromethane is removed in vacuo and the crude material is purified by flash chromatography (silicagel, ethyl acetate/toluene 1:5). The fractions containing 4-phenyl-1-(3-phenylazetidin-1-yl)butan-1-one are collected and the solvent is removed in vacuo to give 467 mg of colorless oil.

Example 27

1-(3-Benzylazetidin-1-yl)-4-phenylbutan-1-on

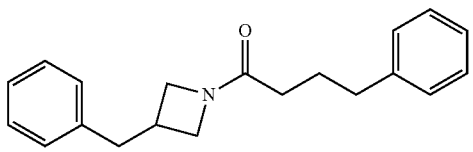 [SMILES: O=C(CCCc1ccccc1)N1CC(Cc2ccccc2)C1]

A solution of 3-benzylazetidine (294 mg, 2 mmol) in dry dichloromethane (6 mL) is cooled in an ice bath, and 4-phenylbutyryl chloride (456.6 mg, 2.5 mmol, 1.25 eq) and triethylamine (417 µL, 3 mmol, 1.5 eq) are added. After stirring for 6 hours at room temperature the reaction mixture is diluted with dichloromethane (10 mL). The organic solution is subsequently washed with 1 M KHSO$_4$, 5% NaHCO$_3$ and brine. After drying over Na$_2$SO$_4$, dichloromethane is removed in vacuo and the crude material is purified by flash chromatography (silicagel, ethyl acetate/toluene 1:5). The fractions containing 1-(3-benzylazetidin-1-yl)-4-phenylbutan-1-one are collected and the solvent is removed in vacuo to give 479 mg of colorless oil.

LCMS ESI⁺: 294.2 (M+H)⁺, $R_t$=1.305 min (LCMS 02).

Example 28

1-(4-Benzylpiperazin-1-yl)pentan-1-one

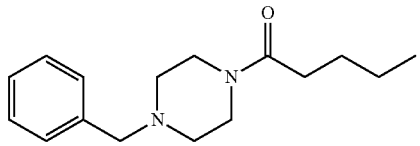 [SMILES: CCCCC(=O)N1CCN(Cc2ccccc2)CC1]

A solution of 1-benzylpiperazine (352 mg, 2 mmol) in dry dichloromethane (6 mL) is cooled in an ice bath, and pentanoyl chloride (301 mg, 2.5 mmol, 1.25 eq) and triethylamine (417 μL, 3 mmol, 1.5 eq) are added. After stirring for 6 hours at room temperature the reaction mixture is diluted with dichloromethane (10 mL). The organic solution is subsequently washed with 1 M KHSO₄, 5% NaHCO₃ and brine. After drying over Na₂SO₄, dichloromethane is removed in vacuo and the crude material is purified by flash chromatography (silicagel, ethyl acetate/toluene 1:1). The fractions containing 1-(4-benzylpiperazin-1-yl)pentan-1-one are collected and the solvent is removed in vacuo to give 416 mg of colorless oil.

LCMS ESI⁺: 261.2 (M+H)⁺, $R_t$=0.705 min (LCMS 01).

Example 29

1-(4-Benzylpiperazin-1-yl)hexan-1-one

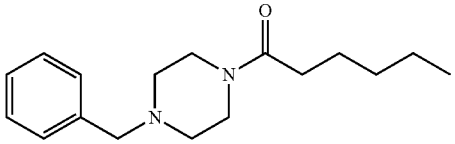 [SMILES: CCCCCC(=O)N1CCN(Cc2ccccc2)CC1]

A solution of 1-benzylpiperazine (352 mg, 2 mmol) in dry dichloromethane (6 mL) is cooled in an ice bath, and hexanoyl chloride (336.5 mg, 2.5 mmol, 1.25 eq) and triethylamine (417 μL, 3 mmol, 1.5 eq) are added. After stirring for 6 hours at room temperature the reaction mixture is diluted with dichloromethane (10 mL). The organic solution is subsequently washed with 1 M KHSO₄, 5% NaHCO₃ and brine. After drying over Na₂SO₄, dichloromethane is removed in vacuo and the crude material is purified by flash chromatography (silicagel, ethyl acetate/toluene 1:1). The fractions containing the 1-(4-benzylpiperazin-1-yl)hexan-1-one are collected and the solvent is removed in vacuo to give 453 mg of colorless oil.

¹H-NMR (D₆-DMSO, 400 MHz) δ: 7.31 (m, 4 H), 7.36 (m, 1 H), 3.44 (m, 2 H), 2.30 (m, 8 H), 1.49 (m, 2 H), 1.26 (broad s, 6 H), 0.85 (t, 3 H).

LCMS ESI⁺: 275.2 (M+H)⁺, $R_t$=0.794 min (LCMS 01).

Example 30

1-(2-Phenylmorpholin-4-yl)pentan-1-one

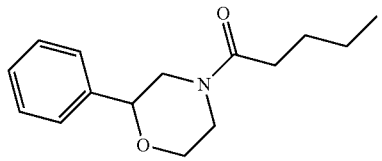 [SMILES: CCCCC(=O)N1CCOC(c2ccccc2)C1]

A solution of 2-phenylmorpholine (326 mg, 2 mmol) in dry dichloromethane (6 mL) is cooled in an ice bath, and pentanoyl chloride (301 mg, 2.5 mmol, 1.25 eq) and triethylamine (417 μL, 3 mmol, 1.5 eq) are added. After stirring for 6 hours at room temperature the reaction mixture is diluted with dichloromethane (10 mL). The organic solution is subsequently washed with 1 M KHSO₄, 5% NaHCO₃ and brine. After drying over Na₂SO₄, dichloromethane is removed in vacuo and the crude material is purified by flash chromatography (silicagel, ethyl acetate/toluene 1:4). The fractions containing 1-(2-phenylmorpholin-4-yl)pentan-1-one are collected and the solvent is removed in vacuo to give 412 mg of colorless oil.

¹H-NMR (D₆-DMSO, 400 MHz) δ: 7.37 (m, 5 H), 4.36 (m, 2 H), 3.98 (bs, 1 H), 3.85 (m, 1 H), 3.55 (m, 1 H), 3.14 (m, 1 H), 2.66 (m, 1 H), 2.35 (m, 2 H), 1.50 (bs, 2 H), 1.32 (bs, 2 H), 0.89 (t, 3 H).

LCMS ESI⁺: 248.2 (M+H)⁺, $R_t$=1.138 min (LCMS 02).

Example 31

1-(2-Phenylmorpholin-4-yl)hexan-1-one

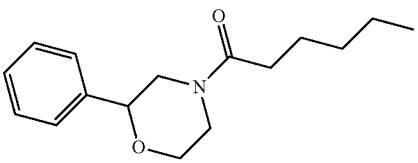 [SMILES: CCCCCC(=O)N1CCOC(c2ccccc2)C1]

A solution of 2-phenylmorpholine (326 mg, 2 mmol) in dry dichloromethane (6 mL) is cooled in an ice bath, and hexanoyl chloride (336.5 mg, 2.5 mmol, 1.25 eq) and triethylamine (417 μL, 3 mmol, 1.5 eq) are added. After stirring for 6 hours at room temperature the reaction mixture is diluted with dichloromethane (10 mL). The organic solution is subsequently washed with 1 M KHSO₄, 5% NaHCO₃ and brine. After drying over Na₂SO₄, dichloromethane is removed in vacuo and the crude material is purified by flash chromatography (silicagel, ethyl acetate/toluene 1:4). The fractions containing 1-(2-phenylmorpholin-4-yl)hexan-1-one are collected and the solvent is removed in vacuo to give 437 mg of colorless oil.

¹H-NMR (D₆-DMSO, 400 MHz) δ: 7.38 (m, 5 H), 4.36 (m, 2H), 3.98 (bs, 1 H), 3.84 (m, 1 H), 3.55 (m, 1 H), 3.13 (m, 1 H), 2.66 (m, 1 H), 2.35 (m, 2 H), 1.51 (bs, 2 H), 1.28 (bs, 4 H), 0.87 (bs, 3 H).

Example 32

1-(3-Phenylpyrrolidin-1-yl)pentan-1-one

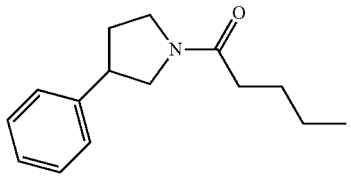 [SMILES: CCCCC(=O)N1CCC(c2ccccc2)C1]

A solution of 3-phenylpyrrolidine (294 mg, 2 mmol) in dry dichloromethane (6 mL) is cooled in an ice bath and pentanoyl chloride (301 mg, 2.5 mmol, 1.25 eq) and triethylamine (417 μL, 3 mmol, 1.5 eq) are added. After stirring for 6 hours at room temperature the reaction mixture is diluted with dichloromethane (10 mL). The organic solution is subsequently washed with 1 M $KHSO_4$, 5% $NaHCO_3$ and brine. After drying over $Na_2SO_4$, dichloromethane is removed in vacuo and the crude material is purified by flash chromatography (silicagel, ethyl acetate/toluene 1:4). The fractions containing 1-(3-phenylpyrrolidin-1-yl)pentan-1-one are collected and the solvent is removed in vacuo to give 378 mg of colorless oil.

$^1$H-NMR ($D_6$-DMSO/$CCl_4$, 400 MHz) δ: 7.26 (m, 5H), 3.84 (m, 1 H), 3.65 (m, 1 H), 3.45 (m, 3 H), 2.23 (broad s, 3 H), 2.00 (m, 1 H), 1.55 (m, 2 H), 1.36 (m, 2 H), 0.95 (m, 3 H).

LCMS ESI$^+$: 232.2 (M+H)$^+$, $R_t$=1.192 min (LCMS 02).

Example 33

1-(3-Phenylpyrrolidin-1-yl)hexan-1-one

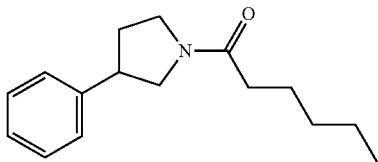 [SMILES: CCCCCC(=O)N1CCC(c2ccccc2)C1]

A solution of 3-phenylpyrrolidine (294 mg, 2 mmol) in dry dichloromethane (6 mL) is cooled in an ice bath, and hexanoyl chloride (336.5 mg, 2.5 mmol, 1.25 eq) and triethylamine (417 μL, 3 mmol, 1.5 eq) are added. After stirring for 6 hours at room temperature the reaction mixture is diluted with dichloromethane (10 mL). The organic solution is subsequently washed with 1 M $KHSO_4$, 5% $NaHCO_3$ and brine. After drying over $Na_2SO_4$, dichloromethane is removed in vacuo and the crude material is purified by flash chromatography (silicagel, ethyl acetate/toluene 1:4). The fractions containing 1-(3-phenylpyrrolidin-1-yl)hexan-1-one are collected and the solvent is removed in vacuo to give 405 mg of colorless oil.

$^1$H-NMR ($D_6$-DMSO/$CCl_4$, 400 MHz) δ: 7.16 (m, 5 H), 3.94 (m, 1 H), 3.60 (m, 1 H), 3.32 (m, 3 H), 2.24 (broad s, 3 H), 1.95 (m, 1 H), 1.52 (m, 2 H), 1.28 (m, 4 H), 0.98 (m, 3 H).

LCMS ESI$^+$: 246.2 (M+H)$^+$, $R_t$=1.274 min (LCMS 02).

The invention claimed is:

1. A pharmaceutical composition comprising a compound of formula

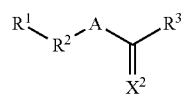

1 wherein $R^1$ is unsubstituted phenyl or phenyl substituted by one, two or three substituents selected from $C_1$-$C_6$-alkyl, trifluoromethyl, $C_1$-$C_6$-alkoxy, $C_1$-$C_6$-alkylcarbonyl, $C_1$-$C_6$-alkylcarbonyloxy, $C_1$-$C_6$-alkylthio, nitro, amino, $C_1$-$C_6$-alkylamino, di-$C_1$-$C_6$-alkylamino, pyrrolidino, piperidino, morpholino, $C_1$-$C_6$-alkylcarbonylamino, and halogen;

unsubstituted 2-, 3- or 4-pyridyl or 2-, 3- or 4-pyridyl substituted by one or two substituents selected from $C_1$-$C_6$-alkyl, trifluoromethyl, $C_1$-$C_6$-alkoxy, nitro, amino, $C_1$-$C_6$-alkylamino, di-$C_1$-$C_6$-alkylamino, $C_1$-$C_6$-alkylcarbonylamino, and halogen; or unsubstituted indolyl or indolyl substituted by one or two substituents selected from $C_1$-$C_6$-alkyl, trifluoromethyl, $C_1$-$C_6$-alkoxy, nitro, amino, $C_1$-$C_6$-alkylamino, di-$C_1$-$C_6$-alkylamino, $C_1$-$C_6$-alkylcarbonylamino, and halogen;

$R^2$ is $(CH_2)_n$ wherein n is 0, 1, 2, 3 or 4;

$R^3$ is $(CH_2)_m R^{3A}$ wherein m is 0, 1, 2, 3 or 4;

$R^{3A}$ is $CH_3$, $CH(CH_3)_2$, $C(CH_3)_3$, $OCH_3$, OH, $OR^{3B}$, C≡CH, C≡N, unsubstituted phenyl or phenyl substituted by one, two or three substituents selected from $C_1$-$C_6$-alkyl, trifluoromethyl, $C_1$-$C_6$-alkoxy, $C_1$-$C_6$-alkylcarbonyl, $C_1$-$C_6$-alkylcarbonyloxy, $C_1$-$C_6$-alkylthio, nitro, amino, $C_1$-$C_6$-alkylamino, di-$C_1$-$C_6$-alkylamino, pyrrolidino, piperidino, morpholino, $C_1$-$C_6$-alkylcarbonylamino, and halogen;

unsubstituted 2- or 3-furanyl or 2- or 3-furanyl substituted by one or two substituents selected from $C_1$-$C_6$-alkyl, trifluoromethyl, $C_1$-$C_6$-alkoxy, and halogen; or unsubstituted 2- or 3-thienyl or 2- or 3-thienyl substituted by one or two substituents selected from $C_1$-$C_6$-alkyl, trifluoromethyl, $C_1$-$C_6$-alkoxy, and halogen; and wherein $R^{3B}$ is unsubstituted phenyl or phenyl substituted by one, two or three substituents selected from $C_1$-$C_6$-alkyl, trifluoromethyl, $C_1$-$C_6$-alkoxy, $C_1$-$C_6$-alkylcarbonyl, $C_1$-$C_6$-alkylcarbonyloxy, $C_1$-$C_6$-alkylthio, nitro, amino, $C_1$-$C_6$-alkylamino, di-$C_1$-$C_6$-alkylamino, pyrrolidino, piperidino, morpholino, $C_1$-$C_6$-alkylcarbonylamino, and halogen;

A is selected from

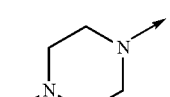

a

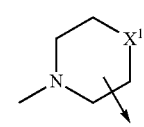

b

-continued

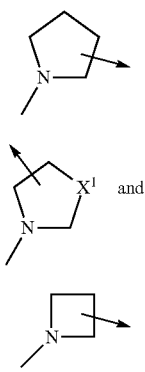

c d e wherein — represents the bond to C(=X²)—R³ and → represents the bond to R²—R¹;
or A together with —C(=X²)—R³ forms a ring selected from

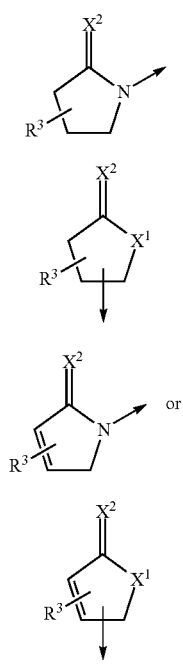

f g h i wherein → represents the bond to R²—R¹;
X¹ is O, S, NH, N(CH₃) or CH₂; and
X² is O, S or NH;
and a compound of formula

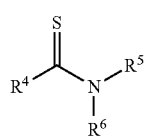

2 wherein R⁴ is optionally substituted phenyl, optionally substituted pyridyl, optionally substituted indolyl, —NR⁷R⁸, or —NH—N=CH—R⁹;

R⁵ is hydrogen, $C_1$-$C_6$-alkyl, optionally substituted phenyl, optionally substituted pyridyl, or a sugar residue;
R⁶ is hydrogen or $C_1$-$C_6$-alkyl, or R⁵ and R⁶ together with the N-atom to which they are bound are pyrrolidine, piperidine or morpholine;
R⁷ is hydrogen, $C_1$-$C_6$-alkyl, optionally substituted phenyl, optionally substituted pyridyl, or a sugar residue;
R⁸ is hydrogen or $C_1$-$C_6$-alkyl, or R⁷ and R⁸ together with the N-atom to which they are bound are pyrrolidine, piperidine or morpholine; and
R⁹ is optionally substituted phenyl,
wherein the sugar residue in R⁵ and R⁷ is L- or D-furanosyl selected from aldopentoses arabinose, lyxose, ribose and xylose of formula 3 below;
L- or D-hexofuranosyl selected from aldohexoses allose, altrose, glucose, mannose, gulose, idose, galactose and talose of formula 4 below;
L- or D-hexofuranosyl selected from ketohexoses fructose, psicose, sorbose and tagatose of formula 5 below;
L- or D-pyranosyl selected from aldohexoses allose, altrose, glucose, mannose, gulose, idose, galctose and talose of formula 6 below; or
L- or D-pyranosyl selected from ketohexoses fructose, psicose, sorbose and tagatose of formula 7 below;

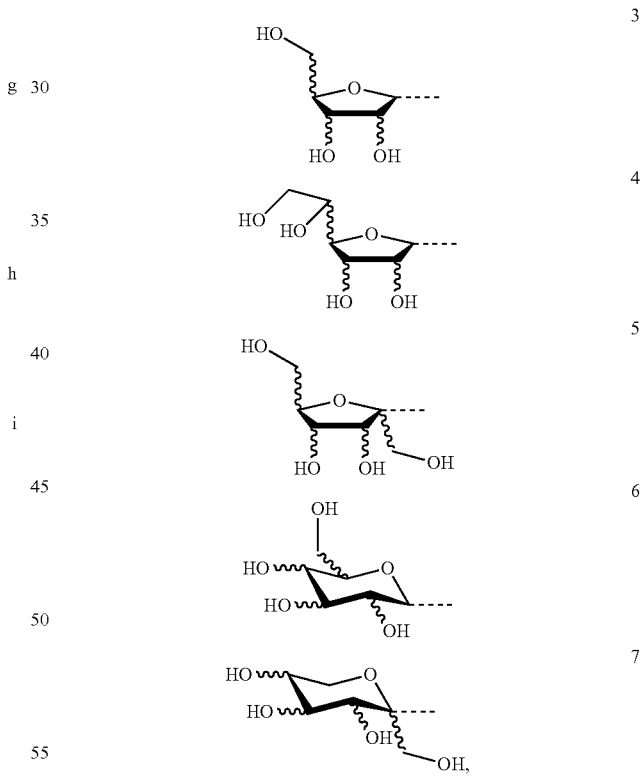

in which one, two, three or four hydroxy groups can be methylated, benzylated or acetylated, or one hydroxy group can be replaced by hydrogen, halogen, methylamino, ethylamino, or acetamido.

2. The pharmaceutical composition according to claim 1 wherein, in the compound of formula 1,
R¹ is
unsubstituted phenyl or phenyl substituted by one, two or three substituents selected from $C_1$-$C_6$-alkyl, trifluoromethyl, $C_1$-$C_6$-alkoxy, $C_1$-$C_6$-alkylcarbonyl, $C_1$-$C_6$- alkylcarbonyloxy, $C_1$-$C_6$-alkylthio, nitro, amino, $C_1$-$C_6$-alkylamino, di-$C_1$-$C_6$-alkylamino, pyrrolidino, piperidino, morpholino, $C_1$-$C_6$-alkylcarbonylamino, and halogen;

unsubstituted 2-, 3- or 4-pyridyl or 2-, 3- or 4-pyridyl substituted by one or two substituents selected from $C_1$-$C_6$-alkyl, trifluoromethyl, $C_1$-$C_6$-alkoxy, nitro, amino, $C_1$-$C_6$-alkylamino, di-$C_1$-$C_6$-alkylamino, $C_1$-$C_6$-alkylcarbonylamino, and halogen; or unsubstituted indolyl or indolyl substituted by one or two substituents selected from $C_1$-$C_6$-alkyl, trifluoromethyl, $C_1$-$C_6$-alkoxy, nitro, amino, $C_1$-$C_6$-alkylamino, di-$C_1$-$C_6$-alkylamino, $C_1$-$C_6$-alkylcarbonylamino, and halogen;

$R^2$ is $(CH_2)_n$ wherein n is 0, 1, 2, 3 or 4;

$R^3$ is $(CH_2)_mCH_3$, $(CH_2)_mOCH_3$, $(CH_2)_mOH$, $(CH_2)_mC\equiv CH$ or $(CH_2)_mC\equiv N$ wherein m is 0, 1, 2 or 3;

A is selected from partial structures a to d and f to i as defined in claim 1;

$X^1$ is O, S, NH, N(CH$_3$) or CH$_2$; and $X^2$ is O, S or NH.

3. The pharmaceutical composition according to claim 1 wherein, in the compound of formula 1, $R^1$ is unsubstituted phenyl or phenyl monosubstituted by one substituent selected from trifluoromethyl, $C_1$-$C_3$-alkoxy, $C_1$-$C_3$-alkylcarbonyl, $C_1$-$C_3$-alkylthio, nitro, amino, $C_1$-$C_3$-alkylamino, and halogen; unsubstituted 2-, 3- or 4-pyridyl or 2-, 3- or 4-pyridyl monosubstituted by one substituent selected from trifluoromethyl, $C_1$-$C_3$-alkoxy, nitro, amino, $C_1$-$C_3$-alkylamino, and halogen; or unsubstituted indolyl or indolyl monosubstituted by one substituent selected from trifluoromethyl, $C_1$-$C_3$-alkoxy, nitro, amino, $C_1$-$C_3$-alkylamino, and halogen;

$R^2$ is $(CH_2)_n$ wherein n is 0, 1 or 2;

$R^3$ is $(CH_2)_mR^{3A}$ wherein m is 0, 1, 2, 3 or 4;

$R^{3A}$ is $CH_3$, $CH(CH_3)_2$, $C(CH_3)_3$, $OCH_3$, OH, $OR^{3B}$, $C\equiv CH$, $C\equiv N$, unsubstituted phenyl or phenyl substituted by one, two or three substituents selected from $C_1$-$C_6$-alkyl, trifluoromethyl, $C_1$-$C_6$-alkoxy, $C_1$-$C_6$-alkylcarbonyl, $C_1$-$C_6$-alkylcarbonyloxy, $C_1$-$C_6$-alkylthio, nitro, amino, $C_1$-$C_6$-alkylamino, di-$C_1$-$C_6$-alkylamino, pyrrolidino, piperidino, morpholino, $C_1$-$C_6$-alkylcarbonylamino, and halogen;

unsubstituted 2- or 3-furanyl or 2- or 3-furanyl substituted by one or two substituents selected from $C_1$-$C_6$-alkyl, trifluoromethyl, $C_1$-$C_6$-alkoxy, and halogen; or unsubstituted 2- or 3-thienyl or 2- or 3-thienyl substituted by one or two substituents selected from $C_1$-$C_6$-alkyl, trifluoromethyl, $C_1$-$C_6$-alkoxy, and halogen; and wherein $R^{3B}$ is unsubstituted phenyl or phenyl substituted by one, two or three substituents selected from $C_1$-$C_6$-alkyl, trifluoromethyl, $C_1$-$C_6$-alkoxy, $C_1$-$C_6$-alkylcarbonyl, $C_1$-$C_6$-alkylcarbonyloxy, $C_1$-$C_6$-alkylthio, nitro, amino, $C_1$-$C_6$-alkylamino, di-$C_1$-$C_6$-alkylamino, pyrrolidino, piperidino, morpholino, $C_1$-$C_6$-alkylcarbonylamino, and halogen;

A is selected from partial structures a to i as defined in claim 1;

$X^1$ is O, S, NH, N(CH$_3$) or CH$_2$; and $X^2$ is O, S or NH.

4. The pharmaceutical composition according to claim 1 wherein, in the compound of formula 1, $R^1$ is unsubstituted phenyl or phenyl monosubstituted by one substituent selected from $C_1$-$C_3$-alkyl, trifluoromethyl, $C_1$-$C_3$-alkoxy, $C_1$-$C_3$-alkylcarbonyl, $C_1$-$C_3$-alkylcarbonyloxy, $C_1$-$C_3$-alkylthio, nitro, amino, $C_1$-$C_3$-alkylamino, di-$C_1$-$C_3$-alkylamino, pyrrolidino, piperidino, morpholino, $C_1$-$C_3$alkylcarbonylamino, and halogen;

unsubstituted 2-, 3- or 4-pyridyl or 2-, 3- or 4-pyridyl monosubstituted by one substituent selected from $C_1$-$C_3$-alkyl, trifluoro methyl, $C_1$-$C_3$-alkoxy, nitro, amino, $C_1$-$C_3$-alkylamino, di -$C_1$-$C_3$-alkylamino, $C_1$-$C_3$-alkyl carbonylamino, and halogen; or unsubstituted indolyl or indolyl monosubstituted by one substituent selected from $C_1$-$C_3$-alkyl, trifluoromethyl, $C_1$-$C_3$-alkoxy, nitro, amino, $C_1$-$C_3$-alkylamino, di-$C_1$-$C_3$-alkylamino, $C_1$-$C_3$ alkylcarbonylamino, and halogen;

$R^2$ is $(CH_2)_n$ wherein n is 0, 1 or 2;

$R^3$ is $(CH_2)_mR^{3A}$ wherein m is 0, 1, 2, 3 or 4;

$R^{3A}$ is $CH_3$, $CH(CH_3)_2$, $C(CH_3)_3$, $OCH_3$, OH, $OR^{3B}$, $C\equiv CH$, $C\equiv N$, unsubstituted phenyl or phenyl substituted by one, two or three substituents selected from $C_1$-$C_6$-alkyl, trifluoromethyl, $C_1$-$C_6$-alkoxy, $C_1$-$C_6$-alkylcarbonyl, $C_1$-$C_6$-alkylcarbonyloxy, $C_1$-$C_6$-alkylthio, nitro, amino, $C_1$-$C_6$-alkylamino, di-$C_1$-$C_6$-alkylamino, pyrrolidino, piperidino, morpholino, $C_1$-$C_6$-alkylcarbonylamino, and halogen;

unsubstituted 2- or 3-furanyl or 2- or 3-furanyl substituted by one or two substituents selected from $C_1$-$C_6$-alkyl, trifluoromethyl, $C_1$-$C_6$-alkoxy, and halogen; or unsubstituted 2- or 3-thienyl or 2- or 3-thienyl substituted by one or two substituents selected from $C_1$-$C_6$-alkyl, trifluoromethyl, $C_1$-$C_6$-alkoxy, and halogen; and wherein $R^{3B}$ is unsubstituted phenyl or phenyl substituted by one, two or three substituents selected from $C_1$-$C_6$-alkyl, trifluoromethyl, $C_1$-$C_6$-alkoxy, $C_1$-$C_6$-alkylcarbonyl, $C_1$-$C_6$-alkylcarbonyloxy, $C_1$-$C_6$-alkylthio, nitro, amino, $C_1$-$C_6$-alkylamino, di-$C_1$-$C_6$-alkylamino, pyrrolidino, piperidino, morpholino, $C_1$-$C_6$-alkylcarbonylamino, and halogen;

A is selected from partial structures a to i as defined in claim 1;

$X^1$ is O, NH, or N(CH$_3$); and $X^2$ is O, S or NH.

5. The pharmaceutical composition according to claim 1 wherein, in the compound of formula 1, $R^1$ is unsubstituted phenyl; unsubstituted 2-, 3- or 4-pyridyl; or unsubstituted indolyl;

$R^2$ is $(CH_2)_n$ wherein n is 0, 1 or 2;

$R^3$ is $(CH_2)_m R^{3A}$ wherein m is 0, 1, 2, 3 or 4;

$R^{3A}$ is $CH_3$, $CH(CH_3)_2$, $C(CH_3)_3$, $OCH_3$, OH, $OR^{3B}$, $C\equiv CH$, $C\equiv N$, unsubstituted phenyl or phenyl substituted by one, two or three substituents selected from $C_1$-$C_6$-alkyl, trifluoromethyl, $C_1$-$C_6$-alkoxy, and halogen;

unsubstituted 2- or 3-furanyl or unsubstituted 2- or 3-thienyl; and wherein $R^{3B}$ is unsubstituted phenyl or phenyl substituted by one, two or three substituents selected from $C_1$-$C_6$-alkyl, trifluoromethyl, $C_1$-$C_6$-alkoxy, and halogen;

A is selected from partial structures a to i as defined in claim 1;

$X^1$ is O, NH, or N(CH$_3$); and $X^2$ is O.

6. The pharmaceutical composition according to claim 1 wherein, in the compound of formula 1, $R^1$ is unsubstituted phenyl; unsubstituted 2-, 3- or 4-pyridyl; or unsubstituted indolyl;

$R^2$ is $(CH_2)_n$ wherein n is 0, 1 or 2;

$R^3$ is $(CH_2)_mCH_3$, $(CH_2)_mC\equiv CH$ or $(CH_2)_mC\equiv N$ wherein m is 2 or 3;

A is selected from partial structures a to d and f to i as defined in claim 1;

$X^1$ is O, NH, or $N(CH_3)$; and $X^2$ is O.

7. The pharmaceutical composition according to claim 1 wherein, in the compound of formula 1, $R^1$ is phenyl or 2-, 3- or 4-pyridyl;

$R^2$ is $(CH_2)_n$ wherein n is 0, 1 or 2;

$R^3$ is $(CH_2)_mR^{3A}$ wherein m is 1, 2, 3 or 4;

$R^{3A}$ is $CH_3$; $CH(CH_3)_2$; $C(CH_3)_3$; $OCH_3$; $OR^{3B}$; unsubstituted phenyl or phenyl substituted by one or two substituents selected from $C_1$-$C_6$-alkyl, trifluoromethyl, $C_1$-$C_6$-alkoxy, and halogen; 2- or 3-furanyl; or 2- or 3-thienyl; and wherein $R^{3B}$ is unsubstituted phenyl or phenyl substituted by one or two substituents selected from $C_1$-$C_6$-alkyl, trifluoromethyl, $C_1$-$C_6$-alkoxy, and halogen;

A is selected from partial structures a to h as defined in claim 1;

$X^1$ is O or NH; and $X^2$ is O.

8. The pharmaceutical composition according to claim 1 wherein, in the compound of formula 1, $R^1$ is phenyl or 2-, 3- or 4-pyridyl;

$R^2$ is $(CH_2)_n$ wherein n is 0, 1 or 2;

$R^3$ is $(CH_2)_mR^{3A}$ wherein m is 1, 2, 3 or 4;

$R^{3A}$ is $CH_3$; $CH(CH_3)_2$; $C(CH_3)_3$; $OCH_3$; $OR^{3B}$; phenyl; 2-furanyl; or 2-thienyl; and wherein $R^{3B}$ is unsubstituted phenyl or phenyl substituted by halogen;

A is selected from partial structures a, b, c, e, f, g, and h as defined in claim 1;

$X^1$ is O or NH; and $X^2$ is O.

9. The pharmaceutical composition according to claim 1, wherein, in the compound of formula 2, $R^4$ is optionally substituted phenyl, optionally substituted pyridyl, optionally substituted indolyl, $-NR^7R^8$; or $-NH-N\!=\!CH-R^9$;

$R^5$ is hydrogen, $C_1$-$C_6$-alkyl, optionally substituted phenyl, optionally substituted pyridyl, or a sugar residue;

$R^6$ is hydrogen or $C_1$-$C_6$-alkyl, or $R^5$ and $R^6$ together with the N-atom to which they are bound are pyrrolidine, piperidine or morpholine;

$R^7$ is hydrogen, $C_1$-$C_6$-alkyl, optionally substituted phenyl, optionally substituted pyridyl, or a sugar residue;

$R^8$ is hydrogen or $C_1$-$C_6$-alkyl, or $R^7$ and $R^8$ together with the N-atom to which they are bound are pyrrolidine, piperidine or morpholine; and $R^9$ is optionally substituted phenyl;

wherein the sugar residue is as defined in claim 1.

10. The pharmaceutical composition according to claim 9, wherein, in the compound of formula 2, $R^4$ is pyridyl substituted by $C_1$-$C_6$-alkyl, $NR^7R^8$, or $-NH-N\!=\!CH-R^9$;

$R^5$ is hydrogen, phenyl substituted by $C_1$-$C_6$-alkoxy, or a sugar residue;

$R^6$ is hydrogen;

$R^7$ is phenyl substituted by $C_1$-$C_6$-alkoxy, or a sugar residue;

$R^8$ is hydrogen; and $R^9$ is phenyl substituted by $C_1$-$C_6$-alkylcarbonylamino.

11. The pharmaceutical composition according to claim 9, wherein the compound of formula 2 is thiacetazone, isoxyl or N-arabinofuranosyl-N'-[p-(isoamyloxy)phenyl]-thiourea.

12. The pharmaceutical composition according to claim 9, wherein the compound of formula 2 is ethionamide.

13. The pharmaceutical composition according to claim 1, wherein the compound of formula 1 and the compound of formula 2 are present in two separate pharmaceutical unit dose forms.

14. A method of treatment of tuberculosis in a warm-blooded animal comprising applying the composition comprising a compound of formula 1 and a compound of formula 2 according to claim 1 to a patient in need thereof.

15. The method according to claim 14, wherein the patient is a human.

* * * * *